US011279753B2

(12) United States Patent
Todaro

(10) Patent No.: US 11,279,753 B2
(45) Date of Patent: *Mar. 22, 2022

(54) USE OF TGF-ALPHA POLYPEPTIDE OR ANTI-TGF-ALPHA ANTIBODIES FOR THE TREATMENT OF DISEASES AND DISORDERS

(71) Applicant: George J. Todaro, Seattle, WA (US)

(72) Inventor: George J. Todaro, Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/693,046

(22) Filed: Nov. 22, 2019

(65) Prior Publication Data

US 2020/0079843 A1   Mar. 12, 2020

Related U.S. Application Data

(63) Continuation of application No. 16/534,691, filed on Aug. 7, 2019, which is a continuation-in-part of application No. PCT/US2018/000021, filed on Feb. 16, 2018.

(60) Provisional application No. 62/460,616, filed on Feb. 17, 2017.

(51) Int. Cl.
| | |
|---|---|
| *A61K 39/395* | (2006.01) |
| *C07K 16/22* | (2006.01) |
| *A61P 35/00* | (2006.01) |
| *A61K 9/00* | (2006.01) |
| *A61K 45/06* | (2006.01) |
| *C07K 16/28* | (2006.01) |

(52) U.S. Cl.
CPC ............ *C07K 16/22* (2013.01); *A61K 9/0019* (2013.01); *A61P 35/00* (2018.01); *A61K 45/06* (2013.01); *C07K 16/2818* (2013.01); *C07K 16/2827* (2013.01)

(58) Field of Classification Search
CPC .......................................... A61K 2039/55522
See application file for complete search history.

(56) References Cited

U.S. PATENT DOCUMENTS

| | | | |
|---|---|---|---|
| 9,575,642 B1 | 6/2017 | Braughler et al. | |
| 2002/0012665 A1* | 1/2002 | Hanna .............. | A61K 39/39541 424/145.1 |
| 2002/0077291 A1 | 6/2002 | Upshall et al. | |
| 2002/0160014 A1 | 10/2002 | Rodriguez et al. | |
| 2003/0138912 A1 | 7/2003 | Busfield et al. | |
| 2013/0131322 A1* | 5/2013 | Kaneda .................. | C07K 16/22 530/388.24 |
| 2014/0343129 A1 | 11/2014 | De et al. | |
| 2019/0375833 A1 | 12/2019 | Todaro | |

FOREIGN PATENT DOCUMENTS

| | | | |
|---|---|---|---|
| WO | WO 1996/025433 A1 | 8/1996 | |
| WO | 03/62395 A2 | 7/2003 | |
| WO | 2006/002203 A2 | 1/2006 | |
| WO | WO2015/176033 | * 11/2015 | |
| WO | 2016/170176 A1 | 10/2016 | |
| WO | WO 2018/151811 A2 | 8/2018 | |

OTHER PUBLICATIONS

Armand P., et al. A phase Ib study of dual PD-1 and CTLA-4 or KIR blockade in patients with relapsed/refractory lymphoid malignancies. Leukemia, 2021, 35:777-786.*
Ciszak, L., et al. Patients with chronic lymphocytic leukemia (CLL) differ in the pattern of CTLA-4 expression on CLL cells: the possible implications for immunotherapy with CTLA-4 blocking antibody. Tumor Biology, 2016, 37:4143-4157.*
Gao, M-Q., et al. Human breast cancer-associated fibroblasts enhance cancer cell proliferation through increased TGF-alpha cleavage by ADAM17. Cancer Letters, 2013, 336:240-246.*
Humphreys, R.C. et al. Transforming growth factor alpha and mouse models of human breast cancer. Oncogene, 2000, 19:1085-1091.*
Joshi, M., et al. Activating the antitumor immune response in non-hodgkin lymphoma using immune checkpoint inhibitors. Journal of Immunology Research, 2020, Article ID 8820377, p. 1-12.*
Li, K., et al. Current molecular targeted therapy in advanced gastric cancer: a comprehensive review of therapeutic mechanism, clinical trials, and practical application. Gastroenterology Research and Practice, 2016, Article ID 4105615, p. 1-9.*
Sun, J., et al. TGF-alpha overexpression in breast cancer bone metastasis and primary lesions and TGF-alpha enhancement of expression of procancer metastasis cytokines in bone marrow mesenchymal stem cells. BioMed Research International, 2018, Article ID 6565393, p. 1-10.*
International Preliminary Report on Patentability received for PCT Patent Application No. PCT/US2018/000021, dated Aug. 29, 2019, 10 pages.
International Search Report and Written Opinion received for PCT Patent Application No. PCT/US2018/000021, dated Aug. 7, 2018, 14 pages.
Lasek et al., "Potentiation Of The Anti-Tumor Effect Of Actinomycin D By Tumor Necrosis Factor Alpha In Mice: Correlation Between In Vitro And In Vivo Results", Int. J. Cancer, vol. 66, May 3, 1996, pp. 374-379.
International Search Report dated Oct. 6, 2020, regarding PCT/US2020/045134.
Xu Quanbin et al: "Human TGFalpha-derived peptide TGFalphaL3 fused with superantigen for immunotherapy of EGFR-expressing tumours." BMC Biotechnology, Biomed Central Ltd., London, GB, vol. 10, No. 1, p. 91 (Dec. 22, 2010).

(Continued)

*Primary Examiner* — Prema M Mertz
(74) *Attorney, Agent, or Firm* — DLA Piper LLP (US)

(57) ABSTRACT

The invention provides a method of treating a disease or disorder in a subject by inducing a TGF alpha immune response or by administering an anti-TGF-alpha antibody or a biologically active fragment thereof. The TGF-alpha immune response is induced using a TGF-alpha polypeptide or biologically active fragment, a vaccine, a genetic construct or a transformed cell, for example.

16 Claims, 8 Drawing Sheets

Specification includes a Sequence Listing.

(56) References Cited

OTHER PUBLICATIONS

Pranav Oberoi et al: "Selective Induction of Cancer Cell Death by Targeted Granzyme B", Antibodies, vol. 2, No. 4, pp. 130-151 (Feb. 27, 2013).
Feng Kaichao et al: "Chimeric antigen receptor-modified T cells for the immunotherapy of patients with EGFR-expressing advanced relapsed/refractory non-small cell lung cancer", Science China Life Sciences, Zhongguo Kexue Zazhishe, China, vol. 59, No. 5, pp. 468-479 (Mar. 11, 2016).
Gregory K. Pennock et al: "New Drug Development and Clinical Pharmacology The Evolving Role of Immune Checkpoint Inhibitors in Cancer Treatment", Oncologist, Jul. 2015; 20(7): 812-822 (Jun. 11, 2015).
Supplementary European Search Report for PCT/US2018/000021 dated Jul. 28, 2020.
EP Office Action in European Application No. 18754645.2, dated May 25, 2021. 5 pages.
Seki et al., "Induction of apoptosis in a human hepatocellular carcinoma cell line by a neutralizing antibody to transforming growth factor-alpha", Virchows Archiv, 430(1):29-35, Jan. 1997.

\* cited by examiner

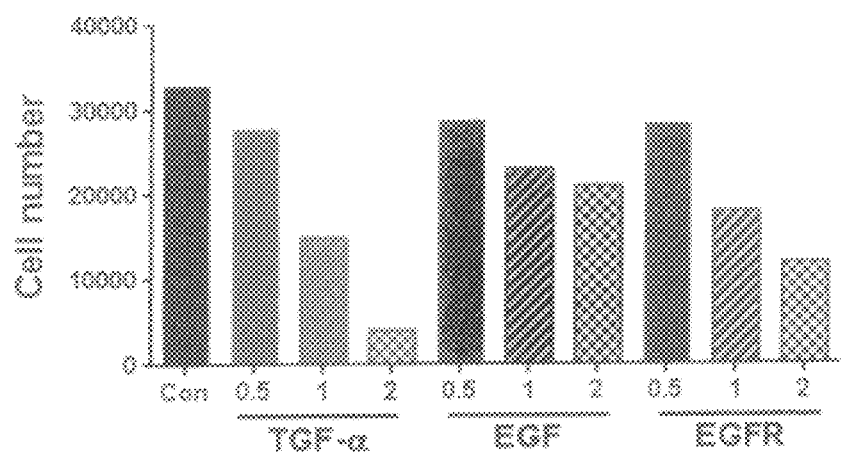
FIG. 7
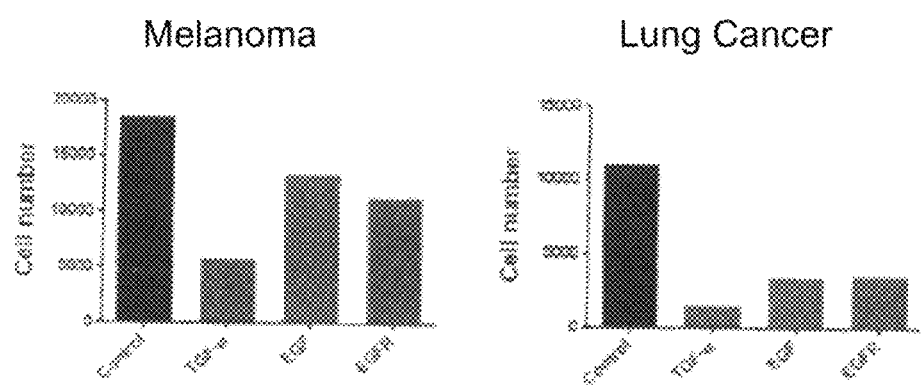
FIG. 8A
FIG. 8B

○ One mouse were found dead

○ 3 mice died after treatment

USE OF TGF-ALPHA POLYPEPTIDE OR ANTI-TGF-ALPHA ANTIBODIES FOR THE TREATMENT OF DISEASES AND DISORDERS

CROSS-REFERENCE TO RELATED APPLICATIONS

This application is a Continuation of U.S. patent application Ser. No. 16/534,691 filed Aug. 7, 2019, which is a Continuation-In-Part of International Patent Application No. PCT/US2018/000021 filed Feb. 16, 2018, which claims priority under 35 USC § 119(e) to U.S. Application Ser. No. 62/460,616 filed Feb. 17, 2017. The disclosure of the prior applications is considered part of and is incorporated by reference in the disclosure of this application in its entirety.

INCORPORATION OF SEQUENCE LISTING

The material in the accompanying sequence listing is hereby incorporated by reference into this application. The accompanying sequence listing text file, name TODARO1100-2_ST25.txt, was created on Nov. 22, 2019, and is 17.5b. The file can be accessed using Microsoft Word on a computer that uses Windows OS.

BACKGROUND OF THE INVENTION

The invention relates generally to growth factors, more specifically to the use of TGF-alpha polypeptide to induce a TGF-alpha specific immune response in a subject, and to the use of anti-TGF-alpha antibodies to target TGF-alpha-producing tumors.

BACKGROUND INFORMATION

The epithelial growth factor receptor EGFR is a transmembrane protein, member of the ErbB family of receptors. Upon binding of one of its specific ligands, the receptor is activated which triggers the receptor's dimerization and auto-phosphorylation, leading to the activation of signaling pathways responsible for cell proliferation, epithelial differentiation and development. Many cancers present EGFR somatic mutation responsible for its duplication or constant activation, resulting in uncontrolled cell division. Along with other growth factors, transforming growth factor TGF alpha (TGF-alpha) and the epithelial growth factor (EGF) are ligands for the EGF receptor; however, TGF-alpha is a much more potent ligand than EGF.

TGF polypeptides are a unique class of proteins distinguishable from other growth factors such as EGF from the standpoint of both biological properties and chemical structure. These TGFs, in turn, possess a variety of properties of value or potential value in the health sciences field including potent, but reversible, cell growth or mitogenic properties which find use in cell repair including, for example, wound healing and ulcer therapy. Additionally, the production of TGF polypeptides, or elevated levels of production, are characteristic of, if not essential to, the morphologic transformation of certain cell lines in both human and murine tissue and/or fluids; therefore, the TGF polypeptides or antigenic fragments thereof are of value in differentiating normal cells from tumor cells and antibodies raised thereto have application in both the diagnosis and treatment of malignancies. Further, realization that certain TGF polypeptides specifically interact with and produce their biological effects through cellular membrane EGF receptors raises the possibility, once the basic TGF polypeptide structure is determined, of correlating its structure with the structure of EGF to develop oligopeptides having chemical characteristics to allow binding to the EGF receptors without concomitant phenotypic transformation of the cell. Oligopeptides having this characteristic EGF receptor binding ability find application in treatment of malignancies, since the oligopeptide will interfere or compete with TGF for available receptor sites and thereby interrupt the expression of the transformed properties of the cell.

When applied to untransformed, non-neoplastic cells growing in culture, TGF-alpha induces changes including a) loss of density-dependent inhibition of cell growth in monolayer culture, b) overgrowth of cells in monolayer culture, c) change in cellular shape, indicating the acquisition of a neoplastic phenotype, and d) acquisition of anchorage-independence, with the resultant ability to grow in soft agar, which highlights cell growth and mitogenic properties. TGF-alpha and EGF share some properties, specifically, the growth factors are both heat-stable, acid-stable peptides, which are sensitive to reducing agents and proteases. Additionally, both TGF-alpha and EGF specifically interact with, and produce biological effects through, EGF receptors with TGF-alpha competing with EGF for binding to the EGF receptor. However, TGF-alpha is distinguishable from EGF, in that EGF does not induce anchorage-independent growth of cells in culture and has only a slight effect on the phenotype of cultured cells, whereas TGF-alpha produces a more pronounced phenotypic alteration in cultured cells and confers on them the ability to behave as transformed cells.

When the sequence of TGF-alpha was determined it was found to have 50 amino acids, 13 of which were identical to epidermal growth factor (EGF). It was found that TGF-alpha and EGF could bind to this same receptor on cells, but that TGF-alpha was much more potent than EGF. The sequences of both were found to depend for their activity by forming 3 disulfide bonds with exactly the same three dimensional pattern. TGF-alpha was primarily produced by tumor cells and could stimulate normal cells to change their morphology to behave like tumor cells. EGF was first recorded in large concentration in mouse salivary glands. TGF-alpha was primarily found in tumor cells; however, it was also expressed in embryos.

Recent reports have shown that EGF has activity when tested with individuals that have lung cancer. However, the effect is not large; most patients still show progressive disease.

Immunotherapy, which aims to actively or passively, induce, enhance or suppress an immune response in a subject, is of great interest in cancer therapy in that it is a powerful tool to stimulate the existing immune response and to target and eliminate cancer cells specifically. Specifically, EGF vaccines, e.g. CIMAVAX™, have been developed that have successfully treated some cancers. Composed of a recombinant human EGF peptide conjugated to a protein carrier, the vaccine aims to immunize lung cancer patients with EGF to induce the production of antibodies targeting self-EGF. Without targeting cancer cells directly, the vaccine targets EGFR's ligand EGF and show some efficiency at reducing EGF concentration in the blood. EGF is one of the main EGFR ligand, along with TGF-alpha. However TGF alpha is a much more potent ligand to EGFR than EGF. Given the efficiency of the existing EGF vaccine, and in regards of the more efficient binding of TGF-alpha to EGFR as compared to EGF, it is suggested that the anti-TGF alpha immune response induced by the TGF-alpha polypeptide or biologically active fragment thereof of the present invention would be more efficient at treating cancer.

SUMMARY OF THE INVENTION

The present invention is based on the seminal discovery that TGF-alpha is a more potent ligand for the EGF receptor as compared to EGF and is therefore useful to induce a TGF-alpha specific immune response in a subject. Specifically, the present invention is based on the induction of a TGF-alpha specific immune response for the treatment of cancer or other diseases and disorders related to TGF-alpha producing cells and/or TGF-alpha ligand/receptor interactions. Additionally, the present invention provides TGF-alpha polypeptides or biologically active fragments thereof, genetic constructs including nucleic acid sequences encoding TGF-alpha polypeptides, vaccines and genetically modified cells that induce a TGF-alpha immune response. TGF-alpha polypeptides and nucleic acid sequences encoding them are known in the art and included herein. Further, the invention provides a method of targeting TGF-alpha-producing tumors by administering anti-TGF-alpha antibody or biologically active fragment thereof.

In one embodiment, the present invention provides a method of treating a TGF-alpha related disease or disorder in a subject comprising administering to the subject a therapeutically effective amount of a TGF-alpha polypeptide or a biologically active fragment thereof. In one exemplary aspect, the TGF-alpha polypeptide or biologically active fragment thereof has at least 75% identity to an amino acid sequence of any of SEQ ID NOs: 5-8, which are splice variants of TGF-alpha or SEQ ID NO:10, the mature protein.

In another aspect, the TGF-alpha polypeptide or biologically active fragment thereof is a fusion protein. In an additional aspect, the TGF-alpha polypeptide or biologically active fragment thereof is genetically modified. In a further aspect, the TGF-alpha polypeptide or biologically active fragment thereof comprises a heterologous sequence. In an additional aspect, the TGF-alpha related disease or disorder is cancer or an immune disorder. In one aspect, the method further comprises the administration of a checkpoint inhibitor or other therapeutic agent, such as a chemotherapeutic agent. In one aspect, the checkpoint inhibitor inhibits PD-1, PD-L1, PD-L2 or CTLA-4.

In another embodiment, the present invention provides a method of treating a TGF-alpha related disease or disorder in a subject comprising inducing the in vivo production of TGF-alpha antibodies in the subject. In one aspect, the method comprises the administration of a TGF-alpha polypeptide or a biologically active fragment thereof. In certain aspects, the TGF-alpha polypeptide has at least 75% sequence identity to the amino acid sequence of any of SEQ ID NOs: 5-8 or 10. In an additional aspect, the TGF-alpha polypeptide or a biologically active fragment thereof is a fusion protein. In a further aspect, the TGF-alpha polypeptide or a biologically active fragment thereof is genetically modified or comprises a heterologous sequence. In another aspect, the method comprises the administration of a TGF-alpha vaccine.

In an additional embodiment, the present invention provides a vaccine for administration to a subject to produce an immune response against TGF-alpha comprising a TGF-alpha polypeptide or a biologically active fragment thereof and optionally an adjuvant. The vaccine composition optionally includes a checkpoint inhibitor, an anti-cancer agent or combinations thereof or other therapeutic molecules.

In a further embodiment, the present invention provides a vaccine for administration to a subject to produce an immune response against TGF-alpha comprising a nucleic acid molecule encoding a TGF-alpha polypeptide or a biologically active fragment thereof and optionally an adjuvant. The vaccine composition optionally includes a checkpoint inhibitor, an anti-cancer agent or combinations thereof or other therapeutic molecules.

In one embodiment, the present invention provides an isolated nucleic acid molecule encoding a chimeric antigen receptor (CAR), wherein the CAR comprises a nucleic acid sequence encoding a TGF-alpha protein or biologically active fragment thereof, a transmembrane domain and an intracellular signaling domain. In an aspect, the transmembrane domain comprises a transmembrane domain of a protein selected from the TGF-alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In an additional aspect, the nucleic acid sequence encoding the TGF-alpha polypeptide or biologically active fragment thereof is connected to the transmembrane domain by a linker or hinge region. A chimeric antigen receptor (CAR) T cell immunotherapeutic agent is an exemplary CAR.

In another aspect, the present invention provides for a chimeric antigen receptor (CAR) polypeptide, wherein the CAR comprises a TGF-alpha protein or biologically active fragment thereof, a transmembrane domain and an intracellular signaling domain.

In an additional aspect, the present invention provides for a method of providing anti-tumor antibodies in a subject, comprising administering to the subject an immune cell comprising a nucleic acid molecule encoding a TGF-alpha polypeptide or biologically active fragment thereof or a TGF-alpha polypeptide or biologically active fragment thereof.

In a further aspect, the present invention provides a pharmaceutical composition comprising a TGF-alpha polypeptide or biologically active fragment thereof and a pharmaceutically acceptable carrier. The pharmaceutical composition optionally includes a checkpoint inhibitor, an anti-cancer agent or combinations thereof or other therapeutic molecules.

In an additional embodiment, the invention provides a method of treating a TGF-alpha related disease or disorder in a subject including administering to the subject a therapeutically effective amount of an anti-TGF-alpha antibody or a biologically active fragment thereof.

In many aspects, the TGF-alpha related disease or disorder is a TGF-alpha-producing tumor. In one aspect, a chemotherapeutic agent, radiation and/or an immune modulator is further administered to the subject, either prior to, simultaneously with or following treatment with the anti-TGF-alpha antibody or biologically active fragment thereof. In another aspect, a checkpoint inhibitor is further administered to the subject. In some aspects, the checkpoint inhibitor inhibits PD-1, PD-L1, PD-L2, CTLA-4 or CD137. In other aspects, the therapeutically effective amount of an anti-TGF-alpha antibody or a biologically active fragment thereof is sufficient to induce a T cell activation in the subject.

In another embodiment, the invention provides a method of inducing T cell activation in a subject comprising administering to said subject a therapeutically effective amount of an anti-TGF-alpha antibody or a biologically active fragment thereof.

In many aspects, the subject has a TGF-alpha producing tumor.

In an additional embodiment, the invention provides a method of treating cancer in a subject including identifying a TGF-alpha-producing tumor from a biological sample from the subject, and administering to the subject a therapeutically effective amount of an anti-TGF-alpha antibody or a biologically active fragment thereof.

In many aspects, a checkpoint inhibitor is further administered. In some aspects, the checkpoint inhibitor inhibits PD-1, PD-L1, PD-L2, CTLA-4 or CD137.

BRIEF DESCRIPTION OF THE DRAWINGS

FIG. 7 shows the number of living cells per well determined by MTS assay in response to various concentrations of TGF-alpha, EGF or EGFR. Con: untreated control; TGF-α: 0.5, 1 or 2 ug/ml of anti-TGF-alpha antibody; EGF: 0.5, 1 or 2 ug/ml of anti-EGF antibody; EGFR: 0.5, 1 or 2 ug/ml of anti-EGFR antibody.

FIGS. 8A and 8B show the number of living cancer cells per well as determined by MTS assay. Specifically, FIG. 8A shows the number of living melanoma cells; Control: untreated control; TGF-α: anti-TGF-alpha antibody; EGF: anti-EGF antibody; EGFR: anti-EGFR antibody. FIG. 8B shows the number of living lung cancer cells; Control: untreated control; TGF-α: anti-TGF-alpha antibody; EGF: anti-EGF antibody; EGFR: anti-EGFR antibody.

FIG. 12A shows the evaluation of the size of the tumors in untreated mice (Control); FIG. 12B shows the evaluation of the size of the tumors in mice treated with anti-TGF-alpha antibodies (TGF-α); FIG. 12C shows the evaluation of the size of the tumors in mice treated with anti-PD-1 antibodies+anti-CTLA4 antibodies (PD-1/CTLA4); and FIG. 12D shows the evaluation of the size of the tumors in mice treated with anti-PD-1 antibodies+anti-CTLA4 antibodies+anti-TGF-alpha antibodies (PD-1/CTLA4/TGF-α).

FIG. 13A shows the evaluation of the size of the tumors in untreated mice (Control); FIG. 13B shows the evaluation of the size of the tumors in mice treated with anti-TGF-alpha antibodies (TGF-α); FIG. 13C shows the evaluation of the size of the tumors in mice treated with anti-PD-1 antibodies (PD-1); and FIG. 13D shows the evaluation of the size of the tumors in mice treated with anti-PD-1 antibodies+anti-TGF-alpha antibodies (PD-1/TGF-α).

DETAILED DESCRIPTION OF THE INVENTION

The present invention is based on the seminal discovery that TGF-alpha is a more potent ligand for the EGF receptor as compared to EGF and therefore may be useful to induce a TGF-alpha specific immune response in a subject. Specifically, the present invention is based on the induction of a TGF-alpha specific immune response for the treatment of cancer or other diseases related to TGF-alpha producing cells and/or TGF-alpha ligand/receptor interactions. Additionally, the present invention provides TGF-alpha polypeptides or biologically active fragments thereof, genetic constructs including nucleic acid sequences encoding TGF-alpha polypeptides, vaccines and genetically modified cells that induce a TGF-alpha immune response. Further, the invention provides a method of targeting TGF-alpha-producing tumors by administering anti-TGF-alpha antibody or biologically active fragment thereof.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

In one embodiment, the present invention provides a method of treating a TGF-alpha related disease or disorder in a subject comprising administering to the subject a therapeutically effective amount of a TGF-alpha polypeptide or a biologically active fragment thereof.

Figures 1, 2:
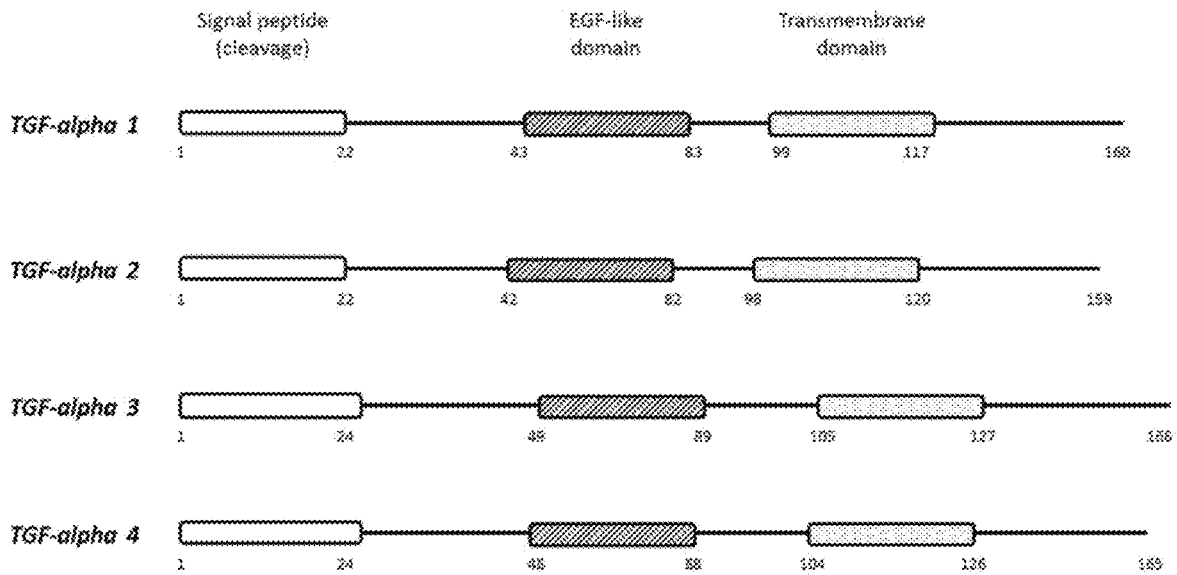
FIG. 1 shows a diagram of four TGF-alpha amino acid sequence splice variants.
FIG. 2 shows a sequence comparison of four TGF-alpha amino acid splice variants (SEQ ID NOs: 5-8).

Transforming growth factor alpha (TGF-alpha or TGF a) is a member of the epidermal growth factor (EGF) family. The human TGF A gene encodes four protein-coding splice variants (see SEQ ID NOs: 5-8) which are encoded by four propeptides or precursor protein nucleic acid sequences (see SEQ ID NOs:1-4). The propeptides are then cleaved to form the mature TGF-alpha protein (see SEQ ID NOs: 9-10). TGF-alpha is a mitogenic polypeptide that is a ligand for the epidermal growth factor receptor EGFR. TGF-alpha is a membrane anchored-growth factor. The precursor is composed of an extracellular domain containing a hydrophobic transmembrane domain, 50 amino acids of the mature TGF-alpha (of which 13 are identical to EGF), and a 35-residue-long cytoplasmic domain. This structure is shared by all the members of the EGF/TGF-alpha family. Both the soluble form (cleaved from the integral membrane glycoprotein by a protease) and the membrane anchored TGF-alpha can bind to and activate EGFR. Both EGF and TGF-alpha bind to EGFR, which induces receptor dimerization and auto-phosphorylation leading to the activation of signaling pathways responsible for cell proliferation, epithelial differentiation and development; however, the ligand recognition involves different amino acid motifs. Additionally, TGF-alpha is a more potent ligand for EGFR compared to EGF. It is to be noted that TGF-alpha and TGF-beta are not structurally or genetically related to one another and act through different receptor mechanisms. There are four different nucleotide and amino acid sequences identified for TGF-alpha corresponding to the four protein-coding splice variants of TGF-alpha (see FIGS. 1-2 and Table 4). It is understood that other nucleic acid or amino acid sequences known to those of skill in the art as TGF-alpha are included in the invention. SEQ ID NOs: 1-10 are provided herein as exemplary molecules and are not meant to be limiting. TGF-alpha sequences are well known to those of skill in the art.

The terms "peptide" and "polypeptide" are used interchangeably herein and refer to any chain of at least two amino acids, linked by covalent chemical bound. As used herein polypeptide can refer to the complete amino acid chain forming a protein or to a fragment thereof.

The term "fragment" refers to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "fragment" of a structure such as an amino acid sequence preferably comprises portions of TGF-alpha polypeptide, or portions of anti-TGF-alpha antibody.

The term "biologically active fragment" as used herein refers to a fragment of a polypeptide which still contains a specific biological activity of said polypeptide. In the context of the present invention, a "biologically active fragment" of TGF-alpha is a fragment of the TGF-alpha polypeptide that is able to induce an immune response in a subject, e.g. bind to EGFR or induce the production of anti-TGF-alpha antibodies.

The amino acid sequence of the TGF-alpha polypeptides and biologically active fragments may comprise 50%, 60%, 70%, 75%, 80%, 85%, 90%, 91%, 92%, 93%, 94%, 95%, 96%, 97%, 98%, 99% or 100% sequence identity to SEQ ID NOs: 5-8 and 10 (mature species). The nucleic acid sequence encoding TGF-alpha polypeptides and biologically active fragments may comprise 50%, 60%, 70%, 75%, 80%, 85%, 90%, 91%, 92%, 93%, 94%, 95%, 96%, 97%, 98%, 99% or 100% sequence identity to SEQ ID NOs: 1-4 and 9 (mature species). The amino acid sequence of the TGF-alpha polypeptides or biologically active fragments and/or nucleic acid sequence encoding such may be genetically modified by modifying, mutating, inserting or deleting one or more amino acids or nucleotides. Methods for genetically modifying amino acids or nucleic acids are known generally in the art and include error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GENE SITE SATURATION MUTAGENESIS™ (GSSM™), synthetic ligation reassembly (SLR) or a combination thereof. In another aspect, the modifications, additions or deletions are introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation and a combination thereof. Additionally, TGF-alpha polypeptides or biologically active fragments or the nucleic acid sequence encoding such may further comprise heterologous amino acid or nucleic acid sequence.

The terms "fusion molecule" and "fusion protein" are used interchangeably and are meant to refer to a biologically active polypeptide, e.g., a TGF alpha or an antibody or a fragment thereof (e.g., Fc region), with or without a further effector molecule usually a protein or peptide sequence covalently linked (i.e. fused) by recombinant, chemical or other suitable method. If desired, the fusion molecule can be used at one or several sites through a peptide linker sequence. Alternatively, the peptide linker may be used to assist in construction of the fusion molecule. Specifically preferred fusion molecules are fusion proteins. Generally fusion molecule also can include conjugate molecules.

Fc-Fusion proteins (also known as Fc chimeric fusion protein, Fc-Ig, Ig-based Chimeric Fusion protein and Fc-tag protein) are composed of the Fc domain of IgG genetically linked to a peptide or protein of interest. Fc-Fusion proteins have become valuable reagents for in vivo and in vitro research. The Fc-fused binding partner can range from a single peptide, a ligand that activates upon binding with a cell surface receptor, signaling molecules, the extracellular domain of a receptor that is activated upon dimerization or as a bait protein that is used to identify binding partners in a protein microarray. One of the most valuable features of the Fc domain in vivo, is it can dramatically prolong the plasma half-life of the protein of interest, which for biotherapeutic drugs, results in an improved therapeutic efficacy; an attribute that has made Fc-Fusion proteins attractive bio-therapeutic agents.

TGF alpha Fc fusion proteins of the invention include the human TGF alpha polypeptide or a biologically active fragment thereof, fused at the 3' end to a human Ig Fc sequence. The Fc fusion proteins would be produced in host cells grown in appropriate medium and purified by affinity chromatography columns. Control human Ig protein from will be used. Suitable cells for the production of the protein fusion are well known but skilled artisans in the art, and can for example be 293T cells, transfected with an expression vector coding for human a TGF alpha or a biologically active fragment thereof, a linker, and a human Ig Fc.

The Fc fragment of the fusion protein of the invention could be selected from the group consisting of IgA, IgG, IgD, IgE and IgM. In a preferred embodiment the protein fusion of the invention would be comprises human TGF alpha protein or a biologically active fragment thereof and an Fc protein of an IgG. Specifically it could be selected from the group consisting of IgG1, IgG2, IgG3 and IgG4.

The term "linker", as used herein, refers to a short peptide sequence that occurs between protein domains or protein fragment to be fused. Linkers are often composed of flexible residues like glycine and serine so that the adjacent protein domains are free to move relative to one another. Longer linkers are used when it is necessary to ensure that two adjacent domains do not sterically interfere with one another. As described in Chen X, et al., (Fusion Protein Linkers: Property, Design and Functionality. Advanced drug delivery reviews. 2013; 65(10):1357-1369. doi:10.1016/j.addr.2012.09.039) many linkers are well known in the art and the choice of a linker depends on several criteria including the type of fusion protein and the type of linker (rigid or flexible). The linker of the present invention would be a short flexible sequence to increase stability and folding of the fusion protein.

The terms "treatment" and "treating" are used interchangeably herein with the term "therapeutic method" and refers to both 1) therapeutic treatments or measures that cure, slow down, lessen symptoms of, and/or halt progression of a diagnosed pathologic conditions or disorder, and 2) prophylactic/preventative measures. Those in need of treatment may include individuals already having a particular medical disorder as well as those who may ultimately acquire the disorder (i.e., those needing preventive measures). Treatment includes monotherapy approaches or combination therapy, for example, use of a TGF-alpha vaccine or of an anti-TGF-alpha antibody, alone or in combination with other therapeutic regimens. TGF-alpha therapy can be prior to, simultaneously with, or following other therapies, e.g., immunosuppressive therapy, chemotherapy, radiotherapy and the like. The TGF-alpha therapies described herein can be prior to or following tumor resection, for example.

The terms "effective dose", "therapeutically efficient dose", "effective amount", therapeutically effective amount" and the like mean the amount of the subject compound that results in either amelioration of symptoms in a subject or a desired biological outcome (biological or medical response of a tissue, system, animal or human that is being sought by the researcher, veterinarian, medical doctor or other clinician). Specifically, such amount should be sufficient to induce a TGF-alpha immune response, e.g., induce the production of anti-TGF-alpha antibodies; or induce T cell activation.

The terms "administration of" and or "administering" should be understood to mean providing a composition in a therapeutically effective amount to the individual in need of treatment. Administration route is not specifically limited and can include oral, intravenous, intramuscular, infusion, intrathecal, intradermal, subcutaneous, sublingual, buccal, rectal, vaginal, ocular, optic route, nasal, inhalation, nebulization, cutaneous, topical, transdermal, intraperitoneal or intratumoral administrations.

As used herein the term "TGF-alpha related disease or disorder" refers to any condition that would benefit from treatment with a TGF-alpha polypeptide or biologically active fragment thereof, a vaccine, a transformed cell, an anti-TGF-alpha antibody or a biologically active fragment thereof. Examples of diseases and disorders include cancer, immune and inflammatory diseases and disorders.

In some aspects, the TGF-alpha related disease or disorder is cancer or an immune disorder. Specifically, the TGF-alpha related disease or disorder is a TGF-alpha-producing tumor.

The term "cancer" refers to a group diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof.

"Cancer cell" or "tumor cell", and grammatical equivalents refer to the total population of cells derived from a tumor or a pre-cancerous lesion, including both non tumorigenic cells, which comprise the bulk of the tumor population, and tumorigenic stem cells (cancer stem cells).

Exemplary cancers include, but are not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood;

Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood'; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland'Cancer, Childhood; Sarcoma, Ewing's Family of Tumors; Sarcoma, Kaposi's; Sarcoma (OsteosarcomaVMalignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In certain aspects, the method is directed at treating cancers selected from lung, stomach, prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, melanoma and urogenital tract. In a preferred embodiment, the invention involves treating cancers that are epithelial tumors such as colon, stomach, lung (e.g., NSCLC), and head and neck cancer.

In other aspects, the method is directed at treating TGF-alpha-producing tumors. In the context of the present invention, "TGF-alpha-producing tumor" refers to tumor that produces and/or releases TGF-alpha. Depending on their specific genetic profile and/or genetic alterations, virtually all tumor can be TGF-alpha-producing, as long as a TGF-alpha production and/or release can be detected and measured. Examples of TGF-alpha-producing tumors include, but are not limited to, lung tumors, ovarian tumors, and melanoma.

In another aspect, the method further comprises administering to the subject a chemotherapeutic agent and/or radiation either prior to, simultaneously with or following treatment with the TGF alpha polypeptide or biologically active fragment thereof. In some aspects several cancer treatments can be used in "combination therapy", or "in combination". The phrases "combination therapy", "combined with" and the like refer to the use of more than one medication or treatment simultaneously to increase the response. The TGF-alpha polypeptide or biologically active fragment thereof, vaccine, genetically modified or transformed cell, or anti-TGF-alpha antibody of the present invention might for example be used in combination with other drugs or treatment in use to treat cancer. Specifically the administration of TGF-alpha polypeptide or biologically active fragment thereof, vaccine, transformed cell, or anti- TGF-alpha antibody to a subject can be in combination with chemotherapy, radiation, or administration of a therapeutic antibody (e.g., ERBITUX™, TARCEVA™, IRESSA™ and TYKERB™) for example. Such therapies can be administered prior to, simultaneously with, or following administration of TGF alpha polypeptide or biologically active fragment thereof, vaccine, transformed cell thereof, or anti-TGF-alpha antibody. TGF-alpha therapy can be prior to, simultaneously with, or following other therapies, e.g., immunosuppressive therapy, chemotherapy, radiotherapy and the like. TGF-alpha therapy described herein can be prior to or following tumor resection, for example.

The term "chemotherapeutic agent" as used herein refers to any therapeutic agent having antineoplastic effect and used to treat cancer. In certain aspects, a chemotherapeutic agent, is a cytotoxic drug, an immunotherapeutic agent or radiation.

Examples of chemotherapeutic agents include, but are not limited to, Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fiuorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, ERBITUX™ (cetuximab), matuzumab, IMC-IIF 8, THERACIM HR3™, denosumab, AVASTIN™ (bevacizumab), HUMIRA™ (adalimumab), HERCEPTIN™ (trastuzumab), REMICADE™ (infliximab), rituximab, SYNAGIS™ (palivizumab), MYLOTARG™ (gemtuzumab oxogamicin), RAPTIVA™ (efalizumab), TYSABRI™ (natalizumab), ZENAPAX™ (dacliximab), NEUTROSPEC™ (Technetium (99mTc) fanolesomab), tocilizumab, PROSTASCINT™ (Indium-Ill labeled Capromab Pendetide), BEXXAR™ (tositumomab), ZEVALIN™ (ibritumomab tiuxetan (IDEC-Y2B8) conjugated to yttrium 90), XOLAIR™ (omalizumab), MABTHERA™ (Rituximab), REOPRO™ (abciximab), MABCAMPATH™ (alemtuzumab), SIMULECT™ (basiliximab), LEUKOSCAN™ (sulesomab), CEA-SCAN™ (arcitumomab), VERLUMA™ (nofetumomab), PANOREX™ (Edrecolomab), alemtuzumab, CDP 870, natalizumab, GILOTRIF™ (afatinib), LYNPARZA™ (olaparib), PERJETA™ (pertuzumab), OPDIVO™ (nivolumab), BOSULIF™ (bosutinib), CABOMETYX™ (cabozantinib), OGIVRI™ (trastuzumab-dkst), SUTENT™ (sunitinib malate), ADCETRIS™ (brentuximab vedotin), ALECENSA™ (alectinib), CALQUENCE™ (acalabrutinib), YESCARTA™ (ciloleucel), VERZENIO™ (abemaciclib), KEYTRUDA™ (pembrolizumab), ALIQOPA™ (copanlisib), NERLYNX™ (neratinib), IMFINZI™ (durvalumab), DARZALEX™ (daratumumab), TECENTRIQ™ (atezolizumab), Avelumab (BAVENCIO™), Durvalumab (IMFINZI™), Iplimumab (YERVOY™) and TARCEVA™ (erlotinib). Examples of immunotherapeutic agent include, but are not limited to, interleukins (11-2, 11-7, 11-12), cytokines (Interferons, G-CSF, imiquimod), chemokines (CCL3, CC126, CXCL7), immunomodulatory imide drugs (thalidomide and its analogues), MGA271, lirilumab, and BMS-986016.

Checkpoint inhibitor therapy is a form of cancer treatment currently that uses immune checkpoints which affect immune system functioning. Immune checkpoints can be stimulatory or inhibitory. Tumors can use these checkpoints to protect themselves from immune system attacks. Checkpoint therapy can block inhibitory checkpoints, restoring immune system function. Checkpoint proteins include programmed cell death 1 protein (PDCD1, PD-1; also known as CD279) and its ligand, PD-L1 ligand 1 (PD-L1, CD274), cytotoxic T-lymphocyte-associated protein 4 (CTLA-4), A2AR (Adenosine A2A receptor), B7-H3 (or CD276), B7-H4 (or VTCN1), BTLA (B and T Lymphocyte Attenuator, or CD272), IDO (Indoleamine 2,3-dioxygenase), MR (Killer-cell Immunoglobulin-like Receptor), LAG3 (Lymphocyte Activation Gene-3), TIM-3 (T-cell Immunoglobulin domain and Mucin domain 3), CD137 (or TNFRSF9 or 4-1BB) and VISTA (V-domain Ig suppressor of T cell activation).

Programmed cell death protein 1, also known as PD-1 and CD279 (cluster of differentiation 279), is a cell surface receptor that plays an important role in down-regulating the immune system and promoting self-tolerance by suppressing T cell inflammatory activity. PD-1 is an immune checkpoint and guards against autoimmunity through a dual mechanism of promoting apoptosis (programmed cell death) in antigen-specific T-cells in lymph nodes while simultaneously reducing apoptosis in regulatory T cells (anti-inflammatory, suppressive T cells).

PD-1 has two ligands, PD-L1 and PD-L2, which are members of the B7 family. PD-L1 protein is upregulated on macrophages and dendritic cells (DC) in response to LPS and GM-CSF treatment, and on T cells and B cells upon TCR and B cell receptor signaling, whereas in resting mice, PD-L1 mRNA can be detected in the heart, lung, thymus, spleen, and kidney. PD-L1 is expressed on almost all murine tumor cell lines, including PA1 myeloma, P815 mastocytoma, and B16 melanoma upon treatment with IFN-γ. PD-L2 expression is more restricted and is expressed mainly by DCs and a few tumor lines.

CTLA4 or CTLA-4 (cytotoxic T-lymphocyte-associated protein 4), also known as CD152 (cluster of differentiation 152), is a protein receptor that, functioning as an immune checkpoint, downregulates immune responses. CTLA4 is constitutively expressed in regulatory T cells but only upregulated in conventional T cells after activation—a phenomenon which is particularly notable in cancers. CTLA4 is a member of the immunoglobulin superfamily that is expressed by activated T cells and transmits an inhibitory signal to T cells. CTLA4 is homologous to the T-cell co-stimulatory protein, CD28, and both molecules bind to CD80 and CD86, also called B7-1 and B7-2 respectively, on antigen-presenting cells. CTLA-4 binds CD80 and CD86 with greater affinity and avidity than CD28 thus enabling it to outcompete CD28 for its ligands. CTLA4 transmits an inhibitory signal to T cells, whereas CD28 transmits a stimulatory signal. CTLA4 is also found in regulatory T cells and contributes to its inhibitory function. T cell activation through the T cell receptor and CD28 leads to increased expression of CTLA-4.

CD137 is a member of the tumor necrosis factor (TNF) receptor family, also referred to as tumor necrosis factor receptor superfamily member 9 (TNFRSF9), 4-1BB and induced by lymphocyte activation (ILA). It is a co-stimulatory immune checkpoint molecule expressed by activated T cells, but to a larger extent on CD8 than on CD4 T cells. In addition, CD137 expression is found on dendritic cells, B cells, follicular dendritic cells, natural killer cells, granulocytes and cells of blood vessel walls at sites of inflammation. CD137 acts as a co-stimulator for activated T cells, with crosslinking of CD137 enhancing T cell proliferation, IL-2 secretion, survival and cytolytic activity. CD137 can also enhance immune activity to eliminate tumors. Utomilumab (PF-05082566) and Urelumab are two non-limiting examples of monoclonal antibodies targeting the receptor to stimulate a more intense immune system attack on cancers cells.

There are several checkpoint inhibitors that are currently used to treat cancer. PD-1 inhibitors include Pembrolizumab (KEYTRUDA™) and Nivolumab (OPDIVO™)). PD-L1 inhibitors include Atezolizumab (TECENTRIQ™)), Avelumab (BAVENCIO™)) and Durvalumab (IMFINZI™)). CTLA-4 inhibitors include Iplimumab (YERVOY™)). There are several other checkpoint inhibitors being developed including an anti B7-H3 antibody (MGA271), an anti-MR antibody (Lirilumab) and an anti-LAG3 antibody (BMS-986016). In certain aspects the chemotherapeutic agent is pembrolizumab, nivolumab, atezolizumab, avelumab, durvalumab, and/or iplimumab. In one aspect, the method further comprising the administration of a checkpoint inhibitor. In another aspect, the checkpoint inhibitor inhibits PD-1, PD-L1, PD-L2 or CTLA-4. In one aspect, the invention methods include administering a TGF-alpha antibody in combination with an anti-PD1 antibody. In another aspect, the invention methods include further administering an anti-CTLA4 antibody. As shown in the Examples (see in particular FIGS. 12 and 13), a therapeutically effective amount of anti-TGF-alpha antibody is from about 50-1000 µg, 100-1000, 200-1000, 250-1000, 250-750 µg/injection and the like. More specifically, a therapeutically effective amount of antibody is from about 250-500 µg/injection. As shown in the Examples, injections may be from about 1-3 times per week. The actual dosage and therapeutic regimen will vary depending on the tumor size, tissue of origin, weight of the subject, and other aspects that can readily be determined by a medical practitioner given the teachings of the present specification.

The compositions of the invention can be used in combination with one or more other anti-cancer therapies, for example, the one or more other anticancer therapies are selected from the group consisting of a cytotoxic chemotherapy, an anti-cancer vaccine, an anti-tumor vaccine, an anti-immunocytokine therapy, an immunocytokine therapy, a checkpoint inhibitor, and a chimeric antigen receptor (CAR) T cell immunotherapeutic agent, and gene transfer therapy.

In an additional aspect, the cancer is a tumor. In certain aspects, the tumor is resected prior to treatment. In yet another aspect, the subject is a human.

As used herein, the term "modulating an immune response" refers to either enhancing or inhibiting an immune response. In some aspects, the TGF-alpha polypeptide or biologically active fragment thereof of the present invention induce or enhance an immune response.

As used herein, the term "modulating TGF-alpha signaling" refers to either increasing or decreasing TGF-alpha signaling. In some aspects, the TGF-alpha polypeptide of biologically active fragment thereof, vaccine or transformed cell of the present invention decreases TGF-alpha signaling.

An immune disease or disorder is a dysfunction of the immune system. These disorders can be characterized in several different ways: by the component(s) of the immune system affected; by whether the immune system is overactive or underactive and by whether the condition is congenital or acquired. Immune diseases and disorders comprise autoimmune diseases or disorders, characterized by the dysfunction of the adaptive immune system, where adaptive immune B and T cells have lost their ability to differentiate self from non-self, and inflammatory diseases or disorders characterized by the dysfunction of the innate immune system, where innate immune cells inappropriately secrete inflammatory molecules such as cytokines.

Immune and inflammatory diseases and disorders include, but are not limited to, Acute disseminated encephalomyelitis (ADEM), Addison's disease, Agammaglobulinemia, Alopecia areata, Amyotrophic lateral sclerosis (aka Lou Gehrig's disease), Ankylosing Spondylitis, Antiphospholipid syndrome, Antisynthetase syndrome, Arthritis, Asthma; Atherosclerosis Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticaria, Autoimmune uveitis, Balo disease/Balo concentric sclerosis, Behçet's disease, Berger's disease, Bickerstaffs encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Discoid lupus erythematosus, Diverticulitis, Dressler's syndrome, Drug-induced lupus, Eczema, Endometriosis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressiva, Fibrosing alveolitis (or Idiopathic pulmonary fibrosis), Gastritis, Gastrointestinal pemphigoid, Glomerulonephritis, Goodpasture's syndrome, graft versus host disease, Gout, Graves' disease, Guillain-Barré syndrome, Hashimoto's encephalopathy, Hashimoto's thyroiditis, Henoch-Schonlein purpura, Hepatitis, Herpes gestationis aka Gestational Pemphigoid, Hidradenitis suppurativa, Hughes-Stovin syndrome, Hypogammaglobulinemi, Idiopathic inflammatory demyelinating diseases, Idiopathic pulmonary fibrosis, Idiopathic thrombocytopenic purpura, IgA nephropathy, Inclusion body myositis, Interstitial cystitis, Irritable bowel syndrome, Juvenile idiopathic arthritis aka Juvenile rheumatoid arthritis, Kawasaki's disease, Lambert-Eaton myasthenic syndrome, Laryngitis, Leukocytoclastic vasculitis, Lichen planus, Lichen sclerosus, Linear IgA disease, Lupoid hepatitis aka Autoimmune hepatitis, Lupus erythematosus, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Myopathies, Meniere's disease, Narcolepsy, Nephritis, Neuromyelitis optica, Neuromyotonia, Occular cicatricial pemphigoid, Opsoclonus myoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Pars planitis, Parsonage-Turner syndrome, Pelvic inflammatory disease, Pemphigus vulgaris, Perivenous encephalomyelitis, Pernicious anaemia, Pharyngitis, Pleurisy, POEMS syndrome, Polyarteritis nodosa, Polymyalgia rheumatica, Polymyositis, Primary biliary cirrhosis, Primary sclerosing cholangitis, Progressive inflammatory neuropathy, Prostatitis, Psoriasis, Psoriatic arthritis, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Rheumatoid arthritis, Sarcoidosis, Schizophrenia, Schmidt syndrome, Schnitzler syndrome, Scleritis, Scleroderma, Seborrheic dermatitis, Serum Sickness, Sinusitis, Sjögren's syndrome, Splenitis, Spondyloarthropathy, Stiff person syndrome, Still's disease, Subacute bacterial endocarditis (SBE), Susac's syndrome, Sweet's syndrome, Sydenham chorea, Sympathetic ophthalmia, Systemic lupus erythematosus, Takayasu's arteritis, Temporal arteritis, Thrombocytopenia, thyroiditis, Tolosa-Hunt syndrome, Transverse myelitis, Ulcerative colitis, Undifferentiated spondyloarthropathy, Urticarial vasculitis, Vasculitis, Vitiligo, Wegener's granulomatosis, Familial Mediterranean fever (FMF), Hyperimmunoglobulinemia D with recurrent fever (HIDS), TNF receptor associated periodic syndrome (TRAPS), Muckle-Wells syndrome (CAPS, urticaria deafness amyloidosis), Familial cold urticarial, Neonatal onset multisystem inflammatory disease, Periodic fever, aphthous stomatitis, pharyngitis and adenitis (PFAPA syndrome), Blau syndrome, Pyogenic sterile arthritis, pyoderma gangrenosum, acne (PAPA), Deficiency of the interleukin-1-receptor antagonist (DIRA), Allergic reactions, Crohn's disease and Gout.

In certain aspects, the immune disorder is Rheumatoid arthritis, Systemic lupus erythematosus, Celiac disease, Crohn's disease, Inflammatory bowel disease, Sjogren's syndrome, Polymyalgia rheumatic, Psoriasis, Multiple sclerosis, Ankylosing spondylitis, Type 1 diabetes, Alopecia areata, Vasculitis, Temporal arteritis, Graves' disease, or Hashimoto's thyroiditis.

In another aspect, the method further comprises administering to the subject an immune modulator either prior to, simultaneously with or following treatment with the TGF-alpha polypeptide or biologically active fragment thereof.

The term "immune modulator" as used herein refers to any therapeutic agent that modulates the immune system. Examples of immune modulators include eicosanoids, cytokines, prostaglandins, interleukins, chemokines, checkpoint regulators, TNF superfamily members, TNF receptor superfamily members and interferons. Specific examples of immune modulators include PGI2, PGE2, PGF2, CCL14, CCL19, CCL20, CCL21, CCL25, CCL27, CXCL12, CXCL13, CXCL-8, CCL2, CCL3, CCL4, CCL5, CCL11, CXCL10, IL1, IL2, IL3, IL4, IL5, IL6, IL7, IL8, IL9, IL10, IL11, IL12, IL13, IL15, IL17, IL17, INF-α, INF-β, INF-ε, INF-γ, G-CSF, TNF-α, CTLA, CD20, PD1, PD1L1, PD1L2, ICOS, CD200, CD52, LTα, LTαβ, LIGHT, CD27L, 41BBL, FasL, Ox40L, April, TL1A, CD30L, TRAIL, RANKL, BAFF, TWEAK, CD40L, EDA1, EDA2, APP, NGF, TNFR1, TNFR2, LTβR, HVEM, CD27, 4-1BB, Fas, Ox40, AITR, DR3, CD30, TRAIL-R1, TRAIL-R2, TRAIL-R3, TRAIL-R4, RANK, BAFFR, TACI, BCMA, Fn14, CD40, EDAR XEDAR, DR6, DcR3, NGFR-p75, and Taj. Other examples of immune modulators include tocilizumab (ACTEMRA™), CDP870 (CIMZIA™), enteracept (ENBREL™), adalimumab (HUMIRA™), Kineret KINERET™, abatacept (ORENCIA™), infliximab (REMICADE™), rituzimab (RITUXAN™), golimumab (SIMPONI™), AVONEX™ REBIF™, RECIGEN™, PLEGRIDY™, BETASERON™, COPAXONE™, NOVATRONE™, natalizumab (TYSABRI™), fingolimod (GILENYA™), teriflunomide (AUBAGIO™), BG12, TECFIDERA™, and alemtuzumab (CAMPATH™, LEMTRADA™).

A used herein, the term "subject," including grammatical variations thereof, refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

In a further aspect, the administration of the TGF-alpha polypeptide or biologically active fragment thereof induces the in vivo production of anti-TGF-alpha antibodies.

As used herein the terms "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. "Antibody," as used herein, refers to an immunoglobulin or immunologically active portions thereof, and encompasses any polypeptide comprising an antigen-binding site regardless of the source, species of origin, method of production, and characteristics. There are five major classes of intact antibodies: IgA, IgD, IgE, IgG, and IgM, and several of these may be further divided into "subclasses" (isotypes), e.g., IgG1, IgG2, IgC3, IgG4, IgA, and IgA2. It includes natural or artificial mono- or polyvalent antibodies including, but not limited to, polyclonal, monoclonal, multispecific, human, humanized or chimeric antibodies, single chain antibodies, or antibody fragments. An antibody as disclosed herein includes an antibody fragment, such as, but not limited to, Fab, Fab' and F(ab')2, Fc, single-chain Fvs (scFv), single-chain antibodies, disulfide-linked Fvs (sdfv) and fragments including either a VL or VH domain. Also includes is a Fc fragment, antigen-Fc fusion proteins, and Fc-targeting moiety.

In a specific embodiment, the administration of the TGF-alpha polypeptide or biologically active fragment thereof, vaccine, transformed cell, or anti-TGF-alpha antibody of the present invention can be intravenous, oral, intramuscular, subcutaneous, intrathecal, infusion, transdermal, sublingual, buccal, rectal, vagina, ocular, optic, nasal, inhalation, nebulization, or cutaneous administration.

In another embodiment, the present invention provides a method of treating a TGF-alpha related disease or disorder in a subject comprising inducing the in vivo production of anti-TGF-alpha antibodies in the subject. In one aspect, the method comprises the administration of a TGF-alpha polypeptide or a biologically active fragment thereof. In certain aspects, the TGF-alpha polypeptide or biologically active fragment thereof has at least 75% sequence identity to the amino acid sequence of any of SEQ ID NOs: 5-8 or 10. In an additional aspect, the TGF-alpha polypeptide or a biologically active fragment thereof is a fusion protein. In a further aspect, the TGF-alpha polypeptide or a biologically active fragment thereof is genetically modified or comprises a heterologous sequence. In another aspect, the method comprises the administration of a TGF-alpha vaccine. In certain aspects, the vaccine is a DNA, RNA or peptide vaccine. In an additional aspect, the method comprises administering a cell transformed with a nucleic acid molecule encoding a TGF-alpha polypeptide or a biologically active fragment thereof. In one aspect, the TGF-alpha related disease or disorder is cancer or an immune disorder.

In a further aspect, the method comprises administering to the subject a chemotherapeutic agent, radiation or immune modulator either prior to, simultaneously with or following treatment with the TGF-alpha polypeptide or biologically active fragment thereof, TGF-alpha vaccine, transformed cell, or anti-TGF-alpha antibody. In certain aspects, the chemotherapeutic agent is pembrolizumab, nivolumab, atezolizumab, avelumab, durvalumab, and/or ipilimumab. In certain aspects, the immune modulator is tocilizumab (ACTEMRA™), CDP870 (CIMZIA™), enteracept (ENBREL™), adalimumab (HUMIRA™), KINERET™, abatacept (ORENCIA™), infliximab (REMICADE™), rituzimab (RITUXAN™), golimumab (SIMPONI™), AVONEX™, REBIF™ RECIGEN™, PLEGRIDY™, BETASERON™, COPAXONE™, NOVATRONE™, natalizumab (TYSABRI™), fingolimod (GILENYA™), teriflunomide (AUBAGIO™), BG12, TECFIDERA™, and alemtuzumab (CAMPATH™, LEMTRADA™). In one aspect, the method further comprising the administration of a checkpoint inhibitor. In another aspect, the checkpoint inhibitor inhibits PD-1, PD-L1, PD-L2 or CTLA-4. In one aspect, the cancer is lung, stomach, prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, or urogenital tract. In an additional aspect, the immune disorder is Rheumatoid arthritis, Systemic lupus erythematosus, Celiac disease, Crohn's disease, Inflammatory bowel disease, Sjogren's syndrome, Polymyalgia rheumatic, Psoriasis, Multiple sclerosis, Ankylosing spondylitis, Type 1 diabetes, Alopecia areata, Vasculitis, Temporal arteritis, Graves' disease or Hashimoto's thyroiditis.

In an additional embodiment, the present invention provides a vaccine for administration to a subject to produce an immune response against TGF-alpha comprising a TGF-alpha polypeptide or a biologically active fragment thereof and optionally an adjuvant.

In a further embodiment, the present invention provides a vaccine for administration to a subject to produce an immune response against TGF-alpha comprising a nucleic acid molecule encoding a TGF-alpha polypeptide or a biologically active fragment thereof and optionally an adjuvant. In one aspect, the nucleic acid is DNA or RNA.

The term "vaccine" refers to a biological preparation that provides an immune response to an antigen. A vaccine typically contains an agent that resembles a disease-causing agent and is often made from weakened or killed forms it, its toxins, or one of its surface proteins. Vaccine stimulates the immune system to recognize the agent as a threat, destroy it, and to further recognize and destroy it in the future. Vaccines can be prophylactic or therapeutic (e.g., cancer vaccines). The term "cancer vaccine" refers to any preparation capable of being used as an inoculation material or as part of an inoculation material, that will provide a treatment for, inhibit and/or convey immunity to cancer and/or tumor growth. A vaccine may be a peptide vaccine, a DNA vaccine or a RNA vaccine for example.

A peptide/polypeptide vaccine including a TGF-alpha polypeptide or biologically active fragment thereof is within the scope of the invention. In one aspect, the vaccine includes an immunogenic amount of a TGF-alpha polypeptide or biologically active fragment thereof of the present invention. The TGF-alpha polypeptide or biologically active fragment thereof of the invention may be conveniently formulated into vaccine compositions including one or more of the peptides alone or in association with a pharmaceutically acceptable carrier.

The vaccine comprises and can be made by providing immunogenic amounts of the peptides alone or in a pharmaceutically acceptable vehicle or carrier. Carriers include water, saline, dextrose, and glycerol, for example. The vaccine can optionally further comprise additional immune-stimulatory molecules and adjuvants or mixture of adjuvants. One of ordinary skill in the art would be able to identify vehicles, carriers, other antigens or immunogens, and immunomodulators, such as adjuvants or cytokines, appropriate for the present invention. Additional additives would also be readily apparent to one of skill in the art, such as wetting agents or preservatives.

The term "adjuvant" refers to a substance used in vaccine preparation to enhance the immune response to an immunogen. There are multiples adjuvant know in the art, however in the U.S., the FDA only approved the use of aluminum salts such as aluminum hydroxide, aluminum phosphate, alum (potassium aluminum sulfate), or mixed aluminum salts, AS04 (combination of aluminum hydroxide and monophosphoryl lipid A, MPL), and AS03 (an oil-in-water emulsion) as adjuvants for vaccines.

A DNA or RNA vaccine is also within the scope of the present invention. One aspect of the invention is a DNA or RNA vaccine comprising DNA or RNA encoding immunoreactive peptides or compositions of the present invention, i.e. TGF-alpha polypeptides or biologically active fragments. Methods for making DNA or RNA sequences suitable for DNA or RNA vaccines are known in the art. One of ordinary skill would be able to determine appropriate promoters or other regulatory sequences which may be used in the DNA or RNA construct encoding the immunoreactive compositions. DNA or RNA vaccines may further comprise other components as in the vaccines and compositions described above and below, such as carriers and agents which increase levels of immunity, such as liposomes. DNA or RNA vaccines may be administered by routes similar to other vaccines. Administration of a DNA or RNA vaccine results in expression of antigens which produce a protective immune response.

The phase "immune response" refers to the body's response originating from the immune system activation by antigens. This process involved several types of immune cells, including antigen presenting cells (APCs), B cells and T cells lymphocytes. Specifically the recombinant TGF-alpha polypeptide or biologically active fragment thereof of the vaccine of the present invention is recognize by the APCs, which activate B cells lymphocytes. With T-helper lymphocytes support, B cells expand, differentiate into mature B cells and ultimately produce anti-TGF-alpha antibodies that uniquely recognize and neutralize autologous TGF-alpha. The term "immunize" refers to eliciting an immune response in an animal, both a humoral immune response and a cellular immune response leading to an immune memory to maintain immunity against said antigen. Specifically, a TGF-alpha immune response refers to an immune response in which anti-TGF-alpha antibodies are produce.

The term "recombinant" or "recombinant TGF-alpha" refers to TGF-alpha proteins resulting from the expression of recombinant DNA (DNA molecules synthesized using laboratory methods of genetic recombination i.e. molecular cloning of the nucleic acid sequence coding for the protein or portion of protein of interest into a plasmid vector.

In one embodiment, the present invention provides an isolated nucleic acid molecule encoding a chimeric antigen receptor (CAR), wherein the CAR comprises a nucleic acid sequence encoding a TGF-alpha protein or biologically active fragment thereof, a transmembrane domain and an intracellular signaling domain. In an aspect, the transmembrane domain comprises a transmembrane domain of a protein selected from the TGF-alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In an additional aspect, the nucleic acid sequence encoding the TGF-alpha polypeptide or biologically active fragment thereof is connected to the transmembrane domain by a linker or hinge region.

The nucleic acid construct of the present invention may be introduced into a cell to be altered thus allowing expression of the chimeric protein within the cell. A variety of cells are known in the art and suitable for recombinant proteins expression. Examples of typical cell used for recombinant protein expression include, but are not limited to, the bacteria E. coli, or the yeast S. cerevisiae.

In another aspect, the present invention provides for a chimeric antigen receptor (CAR) polypeptide, wherein the CAR comprises a TGF-alpha protein or biologically active fragment thereof, a transmembrane domain and an intracellular signaling domain. In one aspect, the transmembrane domain comprises a transmembrane domain of a protein selected from TGF-alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In an additional aspect, the nucleic acid encoding the TGF-alpha polypeptide or biologically active fragment thereof is connected to the transmembrane domain by a linker or hinge region.

In an additional aspect, the present invention provides for a method of providing anti-tumor immunity in a subject, comprising administering to the subject an immune cell comprising a nucleic acid molecule encoding a TGF-alpha polypeptide or biologically active fragment thereof or a TGF-alpha polypeptide or biologically active fragment thereof.

Immunotherapies include the use of adoptive transfer of genetically engineered T cells, modified to recognize and eliminate cancer cells specifically. T cells can be genetically modified to stably express on their surface chimeric antigen receptors (CAR). CAR are synthetic proteins comprising of a signaling endodomain, consisting of an intracellular domain, a transmembrane domain, and an extracellular domain. Upon interaction with the target cancer cell expressing the antigen, the chimeric antigen receptor triggers an intracellular signaling leading to T-cell activation and to a cytotoxic immune response against tumor cells. Such therapies have been shown to be efficient against relapsed/refractory disease. Additionally, CAR-T cells can be engineered to include co-stimulatory receptor that enhances the T-cell-mediated cytotoxic activity. Furthermore, CAR-T cells can be engineered to produce and deliver protein of interest in the tumor microenvironment.

The isolated nucleic acid molecule encoding a CAR of the polypeptide comprising a TGF-alpha protein or biologically active fragment thereof of the present invention will be inserted into a host cell, through the introduction of a vector encoding said polypeptide into said host cell.

The term "nucleic acid" or "nucleic acid construct" is used herein to refer to a recombinant nucleic acid construct that is manipulated by human intervention. A recombinant nucleic acid construct can contain two or more nucleotide sequences that are linked in a manner such that the product is not found in a cell in nature. In particular, the two or more nucleotide sequences can be operatively linked, such as a gene encoding a protein of interest, one or more protein tags, functional domains and the like.

The term "vector" or "cloning vector" or "expression vector" is used herein to refer to a recombinant nucleic acid construct that is manipulated by human intervention. Vectors derived from retrovirus such as lentivirus are suitable tools to achieve long-term gene transfer since they allow long term and stable integration of a transgene and its propagation in daughter cells. The expression vector of the present invention will typically comprise the nucleic acid sequence encoding the CAR polypeptide operably linked to a promoter for the regulation of the expression of said nucleic acid, as well as the typical sequences contained into cloning vectors such as transcription and translation terminators, initiation sequences, an origin of replication functional in at least the target organism, convenient restriction endonucleases, and one or more selectable markers. The cloning vector of the present invention can be selected from the group comprising plasmid, phagemid, phage derivative, virus, and cosmid. Viruses that are useful as vectors include, but are not limited to, retroviruses, adenoviruses, adeno-associated viruses, herpes viruses, and lentiviruses.

As used herein, a "promoter" is intended to mean a polynucleotide sequence capable of facilitating transcription of genes in operable linkage with the promoter. Several types of promoters are well known in the art and suitable for use with the present invention, for example constitutive promoters that allows for unregulated expression in mammalian cells, such as the cytomegalovirus (CMV) promoter. Alternatively, the nucleic acid may include one or more inducible promoters. An inducible promoter is a promoter that, in the absence of an inducer (such as a chemical and/or biological agent), does not direct expression, or directs low levels of expression of an operably linked gene (including cDNA), and, in response to an inducer, its ability to direct expression is enhanced. Exemplary inducible promoters include, for example, promoters that respond to heavy metals, to thermal shocks, to hormones, and those that respond to chemical agents, such as glucose, lactose, galactose or antibiotic.

The vector of the present invention may be physically introduced into a host cell to be altered thus allowing expression of the recombinant CAR protein. A variety of methods are known in the art and suitable for introduction of nucleic acid into a cell, including viral (transduction) and non-viral mediated techniques. Examples of typical non-viral mediated techniques include, but are not limited to, transformation, transfection, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include proprietary transfection reagents such as LIPOFECTAMINE™, DOJINDO HILYMAX™, FUGENE™, JETPEI™, EFFECTENE™ and DREAMFECT™.

The term "host cells", as used herein, refers to the immune cells isolated from a subject in need of the treatment. Prior to expansion and genetic modification, the immune cells can be obtained from several sources including peripheral blood mononuclear cells, bone marrow, lymph node tissue, cord blood, thymus tissue, tissue from an site of infection, ascites, pleural effusion spleen tissue, and tumors. Typically immune cells are isolated from a unit of blood collected from a subject using a number of techniques known to the skilled artisan, such as Ficoll™ separation. The isolated immune cell is selected from the group consisting of an autologous T cell, an allogenic T cell, a T helper cell, a cytotoxic T cell, an effector T cell, a suppressor T cell, a NK cell, a NKT cell or a T cell progenitor cell. T cell population can be isolated and enriched from blood samples using various techniques known in the art (for example U.S. Pat. No. 9,745,368).

Generally, the T cells of the invention are activated and expanded ex vivo, using methods known to the skilled in the art, as described for examples in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,687,041; and U.S. Patent Application No. 20060121005.

Upon isolation from a subject in need, the immune cells, genetically engineered to express a vector encoding a CAR polypeptide comprising a TGF-alpha protein of biologically active fragment thereof, activated and expanded ex vivo, would be administered to the recipient to provide a therapeutic benefit, i.e. induce the production of anti-TGF alpha antibodies thereby inhibiting cancer cells' uncontrolled TGF-alpha-mediated proliferation.

Alternatively, the CAR-T cell encoding a CAR polypeptide comprising a TGF-alpha protein of biologically active fragment thereof and inducing the production of anti-TGF-alpha antibodies could be administered in combination with other anti-tumor therapy to enhance the efficacy of the treatment.

In a further aspect, the present invention provides a pharmaceutical composition comprising a TGF-alpha polypeptide or biologically active fragment thereof, vaccine, transformed cell, or anti-TGF-alpha antibody and a pharmaceutically acceptable carrier.

By "pharmaceutically acceptable" it is meant the carrier, diluent or excipient must be compatible with the other ingredients of the formulation and not deleterious to the recipient thereof.

The compositions for administration will commonly comprise a solution of the peptide or peptide conjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as Remington's Pharmaceutical Science, 19th Ed., Mack Publishing Company, Easton, Pa. (1995).

In an additional embodiment, the invention provides a method of treating a TGF-alpha related disease or disorder in a subject including administering to the subject a therapeutically effective amount of an anti-TGF-alpha antibody or a biologically active fragment thereof.

As used herein, "anti-TGF-alpha antibody" refers to an immunoglobulin or immunologically active portions thereof having an antigen-binding specificity for a TGF-alpha polypeptide, as described in SEQ ID NO.: 5-8 and 10. It is meant to encompass any polypeptide comprising such antigen-binding site regardless of the source, species of origin, method of production, and characteristics. Antibodies include natural or artificial, mono- or polyvalent antibodies including, but not limited to, polyclonal, monoclonal, multispecific, human, humanized or chimeric antibodies, single chain antibodies, and antibody fragments. "Antibody fragments" include a portion of an intact antibody, preferably the antigen binding or variable region of the intact antibody. Examples of antibody fragments include Fab, Fab' and F(ab')2, Fc fragments or Fc-fusion products, single-chain Fvs (scFv), disulfide-linked Fvs (sdfv) and fragments including either a VL or VH domain; diabodies, tribodies and the like (Zapata et al. Protein Eng. 8(10):1057-1062 [1995]).

"Native antibodies" and "intact immunoglobulins", or the like, are usually heterotetrameric glycoproteins of about 150,000 daltons, composed of two identical light (L) chains and two identical heavy (H) chains. The light chains from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The Fab fragment contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')^2$ antibody fragments originally were produced as pairs of Fab' fragments which have hinge cysteines between them. Other chemical couplings of antibody fragments are also known.

The Fc region of an antibody is the tail region of an antibody that interacts with cell surface receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains (CH domains 2-4) in each polypeptide chain. The Fc regions of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues.

Fc-Fusion proteins (also known as Fc chimeric fusion protein, Fc-Ig, Ig-based Chimeric Fusion protein and Fc-tag protein) are composed of the Fc domain of IgG genetically linked to a peptide or protein of interest. Fc-Fusion proteins have become valuable reagents for in vivo and in vitro research. The Fc-fused binding partner can range from a single peptide, a ligand that activates upon binding with a cell surface receptor, signaling molecules, the extracellular domain of a receptor that is activated upon dimerization or as a bait protein that is used to identify binding partners in a protein microarray. One of the most valuable features of the Fc domain in vivo, is it can dramatically prolong the plasma half-life of the protein of interest, which for bio-therapeutic drugs, results in an improved therapeutic efficacy; an attribute that has made Fc-Fusion proteins attractive bio-therapeutic agents.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains which enables the sFv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 [1985]). However, these fragments can now be produced directly by recombinant host cells. For example, the antibody fragments can be isolated from the antibody phage libraries discussed above. Alternatively, Fab'-SH fragments can be directly recovered from $E.$ $coli$ and chemically coupled to form F(ab')$_2$ fragments (Carter et al., Bio/Technology 10:163-167 [1992]). According to another approach, F(ab')$^2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

Monoclonal antibodies can include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 [1984]). Chimeric antibody of interest can include "primatized" antibodies including variable domain antigen-binding sequences derived from a non-human primate (e.g., Old World Monkey, Ape etc) and human constant region sequences; or "humanized" antibodies.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986); Reichmann et al., Nature, 332:323-329 (1988); and Presta, Curr. Op. Struct. Biol., 2:593-596 (1992). The humanized antibody includes a PRIMATIZED™ antibody wherein the antigen-binding region of the antibody is derived from an antibody produced by immunizing macaque monkeys with the antigen of interest.

Methods for humanizing non-human antibodies are well known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 [1988]), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The term "antigen-binding domain" refers to the part of an antibody molecule that comprises the area specifically binding to or complementary to a part or all of an antigen. Where an antigen is large, an antibody may only bind to a particular part of the antigen. The "epitope" or "antigenic determinant" is a portion of an antigen molecule that is responsible for interactions with the antigen-binding domain of an antibody. An antigen-binding domain may be provided by one or more antibody variable domains (e.g., a so-called Fd antibody fragment consisting of a VH domain). An antigen-binding domain may comprise an antibody light chain variable region (VL) and an antibody heavy chain variable region (VH).

Antibodies can be made, for example, via traditional hybridoma techniques, recombinant DNA methods, or phage display techniques using antibody libraries. For various other antibody production techniques, see Antibodies: A Laboratory Manual, eds. Harlow et al., Cold Spring Harbor Laboratory, 1988. However, various anti-TGF-alpha antibodies are commercially available.

The term "biologically active fragment" as used herein refers to a fragment of an antibody which still contains a specific biological activity of said antibody (i.e., its antigen binding specificity). In the context of the present invention, a "biologically active fragment" of an anti-TGF-alpha antibody is any antibody fragment capable of specifically binding to a TGF-alpha polypeptide.

In many aspects, the TGF-alpha related disease or disorder is a TGF-alpha-producing tumor.

In one aspect, a chemotherapeutic agent, radiation and/or an immune modulator is further administered to the subject, either prior to, simultaneously with or following treatment with the anti-TGF-alpha antibody or biologically active fragment thereof.

In another aspect, a checkpoint inhibitor is further administered to the subject. In some aspects, the checkpoint inhibitor inhibits PD-1, PD-L1, PD-L2, CTLA-4 or CD137.

In other aspects, the therapeutically effective amount of an anti-TGF-alpha antibody or a biologically active fragment thereof is sufficient to induce a T cell activation in the subject.

As used herein, "T cell activation" refers to the process through which naïve T cells proliferate, expand and differentiate into effective immune cells. Resting or naïve $CD4^+$ T cells continuously leave the blood and enter secondary lymphoid organs such as spleen, LNs, tonsils, and Peyer's patches, thereby randomly screening the microenvironment. When they encounter an antigen-presenting cell (APC), T cells are activated; they enter a proliferation stage (clonal expansion) and differentiate into effector cells. Differentiated T cells have an important role in controlling and shaping the immune response; they include CD8+ T cells, also known as "killer cells", or "cytotoxic cells", capable to directly kill virus-infected cells as well as cancer cells; CD4+ T cells, or "helper cells", which use cytokine signaling to influence regulatory B cells directly, and other cell populations indirectly; and regulatory T cells that provide the critical mechanism of tolerance, whereby immune cells are able to distinguish invading cells from "self".

In another embodiment, the invention provides a method of inducing T cell activation in a subject comprising administering to said subject a therapeutically effective amount of an anti-TGF-alpha antibody or a biologically active fragment thereof.

In many aspects, the subject has a TGF-alpha producing tumor.

In an additional embodiment, the invention provides a method of treating cancer in a subject including identifying a TGF-alpha-producing tumor from a biological sample from the subject, and administering to the subject a therapeutically effective amount of an anti-TGF-alpha antibody or a biologically active fragment thereof.

As used herein "biological sample" refers to a biopsy of the patient's tumor, or to a biological fluid obtained from the patient. Methods for taking biopsy of a tumor, and/or for collecting biological fluid from a patient are well known in the art, and any standard procedure can be used for obtaining a biological sample from a patient to detect TGF-alpha production and/or release by a tumor. Examples of biological sample or biological fluid include, but are not limited to, tumor biopsy (bone, breast, lung, liver, ovary, prostate melanoma or brain), blood, plasma, urine, bone marrow, and cerebrospinal fluid.

The phrase "identifying a TGF-alpha-producing tumor from a biological sample" refers to determining if the subject has a TGF-alpha-producing tumor, and/or determining if the tumor produces and/or releases TGF-alpha. To determine if a tumor produces TGF-alpha, it requires taking a biopsy from the patient's tumor, and analyzing said tumor protein content to detect the production of TGF-alpha by tumor cells. TGF-alpha release by a tumor may be detected in biological fluids obtained from the patient. TGF-alpha detection and quantification can be assessed by any of the various standard methods of protein detection and quantification that are well known in the art. Such analysis may be performed by using spectrometry methods, such as high-performance liquid chromatography (HPLC) or liquid chromatography-mass spectrometry (LC/MS), and/or antibody dependent methods, such as enzyme-linked immunosorbent assay (ELISA), protein immunoprecipitation, immune-electrophoresis, western blot, or protein immuno staining.

In many aspects, a checkpoint inhibitor is further administered. In some aspects, the checkpoint inhibitor inhibits PD-1, PD-L1, PD-L2, CTLA-4 or CD137.

In various aspects, the method of the present invention includes identifying a TGF-alpha-producing tumor from a biological sample from a patient prior to administering any treatment regimen, as identifying a TGF-alpha-producing tumor is the initial step to identify patients that are candidates for a treatment with the anti-TGF-alpha antibody therapy of the present invention, or with the combination therapy of the present invention, including an anti-TGF-alpha antibody and a checkpoint inhibitor.

Presented below are examples discussing the rational, the potential use of TGF-alpha polypeptides or biologically active fragments and the generation and use of a TGF-alpha vaccine contemplated for the discussed applications.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

Human Cancer Cells Secrete Transforming Growth Factor Alpha

Human cancer cell lines were developed and cultured from lung carcinoma, colon carcinoma, ovary carcinoma, brain carcinoma, and melanoma lesion patient samples. To assess the transforming potential of cancer cell secretion, supernatants collected from the cultured cancer cell lines were applied to previously cultured normal cells. Cancer cell line derived supernatants transformed cultured normal cells to behave like tumor cells. The cancer cell line derived supernatants were purified and sequenced. The results identified two major growth factors: transforming growth factor TGF-alpha (TGF a) and transforming growth factor beta (TGF-β, which is structurally unrelated to TGF-alpha). The sequence of TGF-alpha was found to have 50 amino acids, 13 of which are identical to epidermal growth factor (EGF).

TGF-alpha and EGF both bind to the EGF receptor (EGFR), but TGF-alpha is a much more potent ligand for binding EGFR than EGF. Like EGF, TGF-alpha is a hormone-like protein produced and excreted by many tumors. It was found that upon binding to the EGF receptor, that TGF-alpha, unlike EGF, stimulated cell division, promoted the anchorage-independent growth, thus facilitating tumor growth.

The production of TGF-alpha by transformed cells and the responses of normal cells to the addition of TGF-alpha to the culture medium suggested a TGF-alpha-induced autocrine growth stimulation by rebinding of the released factors at the cell surface. As such, inducing an immune response against TGF-alpha may be a potent cancer therapeutic rationale.

SW1 (melanoma), B16 (melanoma), ID8 (ovarian cancer) and TC1 (lung carcinoma) cancer cell lines from mice origin; and 289 and ovcar 3 (ovarian cancer), 3757 and 3765 (melanoma) and 2756 and 2981 (lung carcinoma) cancer cells lines from human origin were evaluated for their TGF-alpha production. Cells were plated on 2.4 well plates (50,000/well) and incubated for 3 days. The supernatant in each wells was collected and the concentration of TGF-alpha assessed using a TGF-alpha ELISA kit (Biotang, MA, USA).

Figure 3:
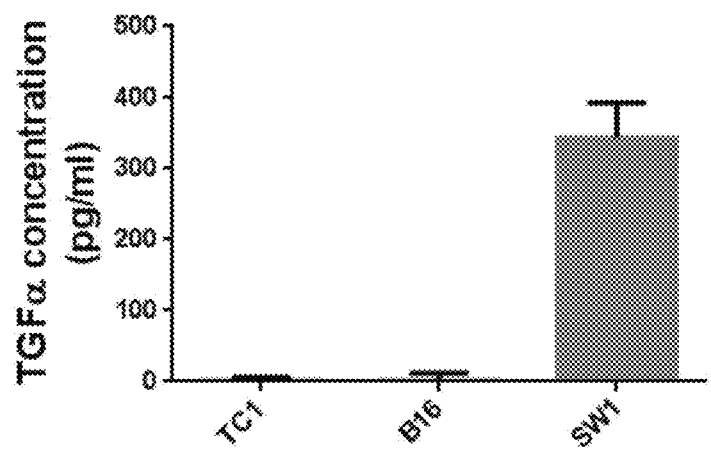
FIG. 3 shows the concentration of TGF-alpha in the supernatant of TC1, B16 and SW1 mouse cancer cells.
Figure 4:
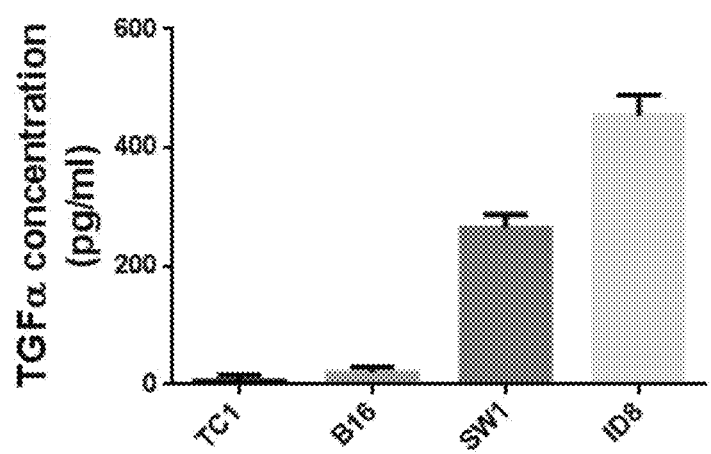
FIG. 4 shows the concentration of TGF-alpha in the supernatant of TC1, B16, SW1 and ID8 mouse cancer cells.

As illustrated in FIG. 3 and FIG. 4, among the rodent cells, melanoma and ovarian cancer cells (SW1 and ID8) were found to produce the highest amounts of TGF-alpha, as compared to the other cell lines tested.

Figure 5:
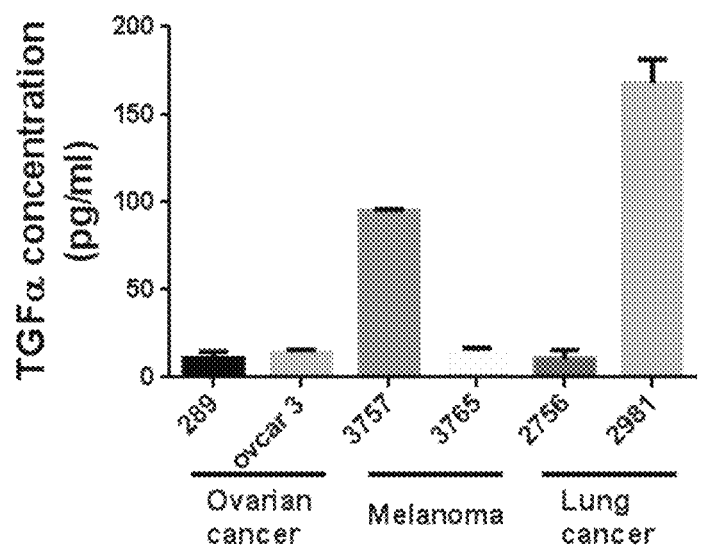
FIG. 5 shows the concentration of TGF-alpha in the supernatant of human cancer cells 289 and ovcar3 (ovarian cancer), 3757 and 3765 (melanoma), and 2756 and 2981 (lung cancer).

As illustrated in FIG. 5, among the human cells, 3575 melanoma cells and 2981 lung cancer cells were found to produce the highest amounts of TGF-alpha as compared to the other cell lines.

Example 2

Evaluation of TGF-Alpha Levels and Bioactivity in Patients' Urine

Many human tumor cell lines express high levels of both TGF-alpha and EGFR. TGF-alpha is primarily found in tumor cells and embryos as well as in many human cancers such as carcinomas of lung, colon, stomach, and head and neck. TGF-alpha presence was evaluated in the urine of 53 subjects comprising 18 apparently health controls, 3 patients with benign conditions (villous colic adenoma, fibrocystic breast and 38 weeks pregnancy), and 32 patients with confirmed cancer diagnostic (13 lung carcinomas, 7 gastro-intestinal carcinomas, 3 urogenital carcinomas, 5 breast carcinomas and 4 lymphoid cancers). As detailed in Table 1, substantially increased levels of TGF-alpha were found in urine from cancer patients as compared to matched controls. Only one apparently healthy control presented increased TGF-alpha urine concentration (6%), the only benign condition presenting elevated TGF-alpha urine concentration was in the pregnancy context, while 81% of the cancer patients had more than a two-fold increase in TGF-alpha urine concentration as compared to the normal value. Interestingly this value ranged from 57% for gastrointestinal carcinomas to up to 100% for certain cancer types (urogenital and breast).

This result indicated that urine can be used as a convenient and readily available material to detect TGF-alpha production and to determine TGF-alpha concentration. Moreover, it illustrated that TGF-alpha measurement might be a useful diagnostic marker to detect certain types of cancer.

TABLE 1

Detection of TGF-alpha antigen in urine

| PATIENT GROUP | OVERALL POSITIVE |
| --- | --- |
| Apparently healthy controls | 1/18 (6%) |
| Patients with benign conditions | 1/3 (33%) |
| colon (villous adenoma) | 0/1 (0%) |
| breast (fibrocystic) | 0/1 (0%) |
| pregnancy (normal, 38 wks) | 1/1 (100%) |
| Patients with cancer | 26/32 (81%) |
| Lung | 11/13 (85%) |
| Gastrointestinal | 4/7 (57%) |
| Urogenital | 3/3 (100%) |
| Breast | 5/5 (100%) |
| Lymphoid | 3/4 (75%) |

Cut off > 2 x average normal value

Further, TGF-alpha bioactivity was evaluated in the urine of 50 subjects comprising 25 normal controls, and 25 patients with confirmed cancer diagnostic (5 lung carcinomas, 5 breast carcinomas, 5 colon carcinomas, 5 melanomas and 5 leukemia). As detailed in Table 2, substantially increased bioactivity of TGF-alpha was found in urine from cancer patients as compared to matched controls. Only one control presented an increased TGF-alpha urine bioactivity (4%), while an average of 64% of the cancer patients had a significantly higher TGF-alpha urine bioactivity as compared to the normal value. Interestingly this value ranged from 0% for leukemia to 80% for lung and breast cancers, and up to 100% for melanomas.

This result indicated that urine is a convenient and readily available material that can be used for the bio-characterization of TGF-alpha bioactivity. Moreover, it illustrated that TGF-alpha bioactivity can be correlated with presence of certain cancers and that TGF-alpha bioactivity measurement might be a useful diagnostic marker to detect certain types of cancer

TABLE 2

Detection of TGF bioactivity in urine of cancer patients

| DIAGNOSIS | NO. POSITIVE/NO. TESTED |
|---|---|
| Lung Cancer | 4/5 (80%) |
| Breast Cancer | 4/5 (80%) |
| Colon Cancer | 3/5 (60%) |
| Melanomas | 5/5 (100%) |
| Leukemia | 0/5 (0%) |
| Normal Conditions | 1/25 (4%) |

Example 3

Evaluation the Effects of TGF-Alpha Treatment on Tumor Cell Growth

In order to assess the effects of TGF-alpha on tumor cell growth (stimulating or inhibiting effects), and to compare them to the effects of EGF, Human squamous carcinoma A431 cells, known for their abnormally high levels of EGFR, were cultured and exposed to various doses of EGF or TGF-alpha. Tumor cell growth in soft agar, spreading and regular growth were evaluated. TGF-alpha was found more efficient at allowing normal cells to grow in soft agar as compared to EGF. TGF-alpha was also found more efficient to allow the cells to spread apart from one another due to increased ruffling of the cell membrane.

TABLE 3

Effect of TGF-alpha and EGF on the growth of human tumor cell line A431

| | Concentration | Cell Numbers/Day 7 ($1 \times 10^5$) |
|---|---|---|
| EGF | 0.1 µg/ml | 12 |
| | 1.0 µg/ml | 46 |
| TGFα | 0.1 µg/ml | 75 |
| | 1.0 µg/ml | 90 |

Example 4

Evaluation of TGF-Alpha Antibodies Effects on In Vitro Colony Formation and Invasiveness To further evaluate the effect of modulating TGF-alpha on tumor cells growth, clonogenic assays (or colony formation assays), invasion assays and migration assays were performed to show that clearing TGF-alpha from the culture media using anti-TGF-alpha antibodies resulted in an effective inhibition of clonogenic: colony formation of cancer cells and an inhibition of invasion and migration by the cancer cells.

During the clonogenic assay, the effectiveness of anti-TGF-alpha antibodies on the survival and proliferation of human cancer cells was assessed and compared to the efficacy of anti-EGF antibodies and anti-EGFR antibodies and control IgG to inhibit cell proliferation. The cells were treated before being plated in tissue culture dishes and allowed to grow. After the period of time required for the cells treated with the control IgG to grow and form colonies, all plates were fixed, colonies stained and counted. The percentage of surviving cells which grew into colonies was evaluated. Comparative cell survival curves were generated to compare the effect of anti-TGF-alpha antibodies to control IgG, anti-EGF antibodies and anti-EGFR antibodies on cell survival.

Comparison of the number of colonies formed following IgG treatment to the number of colonies formed after anti-TGF-alpha treatment shown that anti-TGF-alpha antibodies were potent inhibitors of clonogenic colony formation of human cancer cells. Further, anti-TGF-alpha antibodies were found to be a more potent inhibitor of colony formation that anti EGF antibodies or anti-EGFR antibodies.

The effectiveness of anti-TGF-alpha antibodies on migratory and invasive properties of human cancer cells was assessed by invasion and migration assays, and the efficacy of anti-TGF-alpha antibodies was compared to anti-EGF and anti-EGFR antibodies, as well as to control IgG. The cells were treated before being plated in tissue culture dishes and allowed to migrate through a porous membrane and invade an extracellular matrix. After the period of time required for the cells treated with the control IgG migrate and invade the extracellular matrix, all plates were fixed, cells stained and counted. The percentage of migrating and invasive cells was evaluated and comparative percentages of migratory and invasive cells were established to determine the effect of anti-TGF-alpha antibodies as compared to control IgG, anti-EGF antibodies and anti-EGFR antibodies.

Comparison of the number of migrating and invasive cells after the control IgG treatment to the number of migrating and invasive cells after anti-TGF-alpha treatment shown that anti-TGF-alpha antibodies were potent inhibitors of human cancer cell migration and invasion.

Further, anti-TGF-alpha antibodies were found to be a more potent cancer cell migration and invasion inhibitor than anti-EGF antibodies or anti-EGFR antibodies.

Example 5

Evaluation of the Effect of Recombinant TGF-Alpha and Anti-TGF-Alpha Antibodies on TGF-Alpha-Producing Tumor Cells The effect of recombinant TGF-alpha and of anti-TGF-alpha antibodies (anti-TGF-alpha, anti-EGF, and/or anti-EGFR antibodies) on TGF-alpha-producing cell survival was evaluated. SW1, ID8, B16 and TC1 cells were plated into 96 well plates (10,000 cells/well) and anti-TGF alpha antibodies and/or recombinant TGF-alpha protein were added to the plates. One day after incubation, the cell number in each well was determined in a MTS assay using a CellTiter 96® AQueous One Solution Cell Proliferation Assay (Promega).

Figure 6:
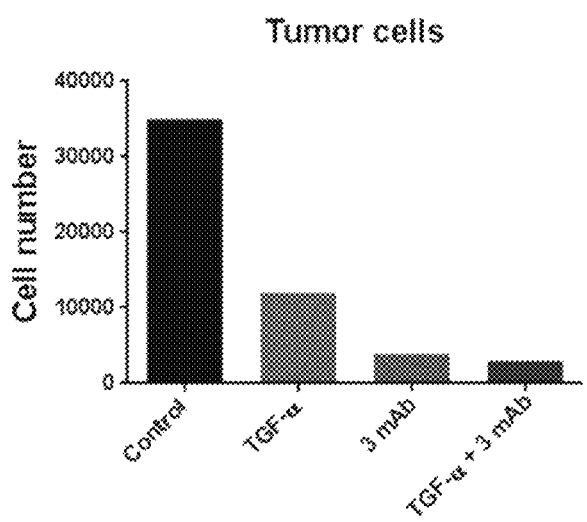
FIG. 6 shows the number of living tumor cells per well determined by MTS assay. Control: untreated cells; TGF-α: recombinant TGF-alpha; 3 mAb: anti-TGF-alpha+anti EGF+anti-EGFR antibodies; TGF-α+3 mAb: recombinant TGF-alpha+anti-TGF-alpha, anti EGF and anti-EGFR antibodies.

As illustrated in FIG. 6, the treatment of the cells with anti-TGF-alpha, anti-EGF and anti-EGFR antibodies was found to be more efficient at reducing the number of living cells than recombinant TGF-alpha protein.

Additionally, and as illustrated in FIG. 7, it was found that the treatment of the cells with anti-TGF-alpha antibodies was more efficient at reducing the number of living cells than the treatment with anti-EGF antibodies or with anti-EGFR antibodies, independently of the dose used.

Example 6

Evaluation of the Effects of Anti-TGF-Alpha, Anti-EGF and Anti-EGFR Antibodies on TGF-Alpha Producing Cells To further evaluate the effect of modulating TGF-alpha on TGF-alpha-producing tumor cells survival, MTS assay were performed on human cells derived from TGF-alpha-producing melanoma and lung cancer.

Melanoma and lung cancer cells were plated into 96 well plates (10,000 cells/well) and anti-TGF-alpha antibodies, anti-EGF antibodies or anti-EGFR antibodies were added to the plates. One day after incubation, the cell number in each well was determined using CellTiter 96® AQueous One Solution Cell Proliferation Assay (Promega).

As illustrated in FIGS. 8A and 8B, the treatment of the cells with anti-TGF-alpha antibodies was found more efficient at reducing the number of living melanoma cells (FIG. 8A) and lung cancer cells (FIG. 8B) as compared to anti-EGF and anti-EGFR antibodies.

Example 7

Use of Anti-TGF-Alpha Antibodies in Mouse Xenograft Tumor Models

Immunodeficient or syngeneic mice were subcutaneously transplanted with human tumor cells known to produce TGF-alpha following a xenograft model approach. Once the cells had developed into palpable tumors of approximately 3 mm mean diameter, each animal (5 in each group) received one injection weekly, for 3 weeks, of 0.5 mg/mouse of an antibody suspension.

Several commercially available antibodies directed against TGF-alpha (monoclonal and polyclonal, of mouse origin, and recognizing the human molecule) were used in order to determine which TGF-alpha epitopes induces the more efficient tumor-inhibitory therapeutic response.

As such, the xenograft models were used to assess the greater efficacy of different TGF-alpha antibodies and epitopes. Specifically, 4 groups of 5 mice were used, receiving respectively a control IgG, anti-TGF-alpha antibodies, anti-EGF antibodies, or anti-EGFR antibodies. Control IgG, anti-TGF-alpha, anti-EGF, and anti-EGFR-antibodies were purchased from the same company (Life Span BioSciences Inc.). This approach identified TGF-alpha epitopes that had greater tumor inhibition efficacy.

To assess the best delivery method, in alternative experiments the antibody injections were performed either intraperitoneally or intratumorally.

Example 8

In Vivo Evaluation of Therapeutic Efficacy of TGF-Alpha Antibodies for the Inhibition of Cancer Cell Growth The efficacy of TGF-alpha antibodies to inhibit the growth of human cancer cells known to produce TGF-alpha was evaluated. Four groups of 5 mice subcutaneously transplanted with TGF-alpha-producing human cancer cells, as described in Example 7 were injected with control IgG antibodies, anti-TGF-alpha antibodies, anti-EGF antibodies, and anti-EGFR antibodies. In alternative experiments, the mice used were either immunodeficient or syngeneic mice, and the antibodies injections were received either intraperitoneally or intratumorally.

Comparison of the control IgG group to the anti-TGF-alpha antibody group shown that anti-TGF-alpha antibodies were highly efficient for the inhibition of the growth of subcutaneously injected human cancer cells known to produce TGF-alpha. Additionally, the comparison of the control IgG group to the anti-EGF and anti-EGFR antibody groups shown the efficacy of using either anti-EGF or anti-EGFR antibodies to inhibit the growth of subcutaneously injected human cancer cells known to produce TGF-alpha (and thus to activate the EGFR pathway).

Furthermore, comparison of the anti TGF-alpha antibody group to either the anti-EGF or the anti-EGFR antibody groups shown that anti-TGF-alpha antibodies were more efficient than both anti-EGF and anti-EGFR antibodies to inhibit the growth of human cancer cells known to produce TGF-alpha.

Example 9

In Vitro Evaluation of TGF-Alpha-Producing Cells Sensitization to Anti-EGF, Anti-EGFR, Anti-TGF-Alpha and/or Anti-Immune Checkpoint Antibodies The efficacy of TGF-alpha antibodies in combination with anti-immune checkpoint antibodies to inhibit the growth of human cancer cells known to produce TGF-alpha was evaluated in vitro in MTS assays.

To evaluate cell sensitization, TGF-alpha-producing cancer cells were plated into 96 well plates (10,000 cells/well) and anti-TGF-alpha, anti-EGF, anti-EGFR, anti-PD-1, anti-CTLA4, and/or anti-CD137 antibodies were added to the plates. After incubation, the cell number in each well was determined using CellTiter 96® AQueous One Solution Cell Proliferation Assay (Promega).

Figure 9:
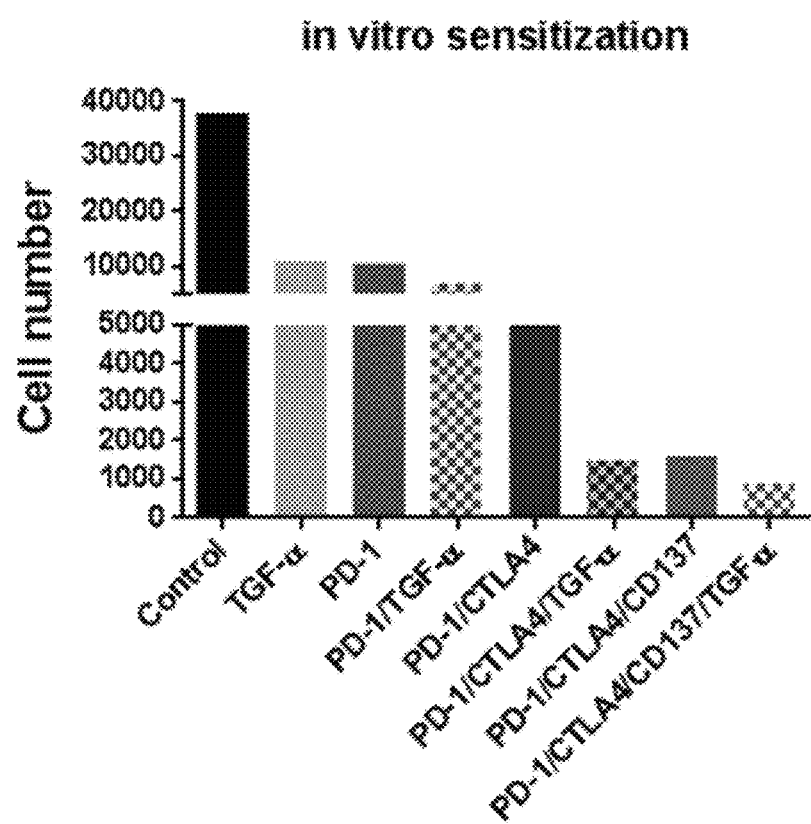
FIG. 9 shows the number of living tumor cells per well determined by MTS assay. Control: untreated cells; TGF-α: anti-TGF-alpha antibody; PD-1: anti-PD-1 antibody; PD-1/TGF-α: anti-PD-1 antibody+anti-TGF-alpha antibody; PD-1/CTLA4: anti-PD-1 antibody+anti-CTLA4 antibody; PD-1/CTLA4/TGF-α: anti-PD-1 antibody+anti-CTLA4 antibody+anti-TGF-alpha antibody; PD-1/CTLA4/CD137: anti-PD-1 antibody+anti-CTLA4 antibody+anti-CD137 antibody; PD-1/CTLA4/CD137/TGF-α: anti-PD-1 antibody+anti-CTLA4 antibody+anti-CD137 antibody+anti-TGF-α antibody.

As illustrated in FIG. 9, it was found that anti-TGF-alpha antibodies alone were potent to reduce the number of living TGF-alpha-producing cancer cells; and that the combination of anti-TGF-alpha antibodies with anti-PD-1, anti-CTLA4 and anti-CD137 antibodies produced a synergic effect resulting in a drastic reduction of cell survival.

Figure 10:
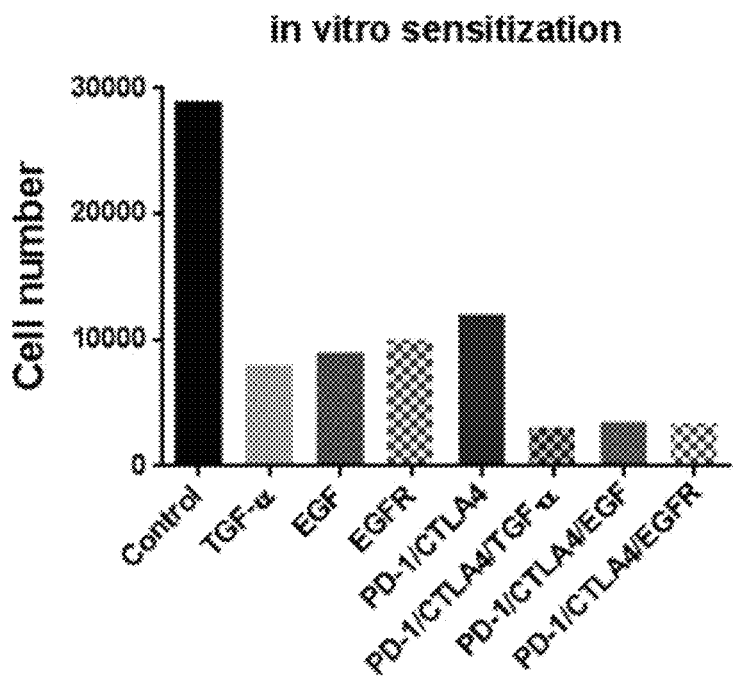
FIG. 10 shows the number of living tumor cells per well determined by MTS assay. Control: untreated cells; TGF-α: anti-TGF-alpha antibody; EGF: anti-EGF antibody; EGFR: anti-EGFR antibody; PD-1/CTLA4: anti-PD-1 antibody+anti-CTLA4 antibody; PD-1/CTLA4/TGF-α: anti-PD-1 antibody+anti-CTLA4 antibody+anti-TGF-alpha antibody; PD-1/CTLA4/EGF: anti-PD-1 antibody+anti-CTLA4 antibody+anti-EGF antibody; PD-1/CTLA4/EGFR: anti-PD-1 antibody+anti-CTLA4 antibody+anti-EGFR antibody.

Further, and as illustrated in FIG. 10, anti-TGF-alpha antibodies, alone or in combination with antibodies directed against an immune checkpoint protein (PD-1 and/or CTLA4) were found more potent at reducing TGF-alpha-producing cancer cell survival as compared to anti-EGF and anti-EGFR antibodies.

Example 10

In Vivo Evaluation of Therapeutic Efficacy of TGF-Alpha Antibodies in Combination with Anti-Immune Checkpoint Antibodies The efficacy of TGF-alpha antibodies in combination with anti-immune checkpoint antibodies to inhibit the growth of human cancer cells known to produce TGF-alpha was evaluated in vivo. Eight groups of 5 mice, subcutaneously transplanted with TGF-alpha-producing human cancer cells as described in Example 7, were treated with control IgG antibodies, anti-TGF-alpha antibodies, anti-EGF antibodies, anti-EGFR antibodies, control IgG antibodies+anti-PD-1 antibodies, anti-TGF-alpha antibodies+anti-PD-1 antibodies, anti-EGF antibodies+anti-PD-1 antibodies, and anti-EGFR antibodies+anti-PD-1 antibodies, respectively. In alternative experiments, the mice used were either immunodeficient or syngeneic mice, and the antibodies injections were received either intraperitoneally or intratumorally.

Comparison of the control IgG group to the anti TGF-alpha antibody group shown that anti-TGF-alpha antibodies are highly efficient to inhibit the growth of human cancer cells known to produce TGF-alpha. Comparison of the control IgG group to the anti-EGF and anti-EGFR antibody groups shown the efficacy of using either anti-EGF or anti-EGFR antibodies to inhibit the growth of human cancer cells (and thus to activate the EGFR pathway). Comparison of the control IgG group and the control IgG+anti-PD-1 group shown the efficacy of the anti-PD-1 antibodies to inhibit the growth of human cancer cells. Comparison of the anti-EGF and anti-EGFR antibody groups and the anti-EGF+anti-PD-1 antibody and anti-EGFR+anti-PD-1 antibody groups demonstrated the benefits of combining anti-PD-1 antibodies to anti-EGF or anti-EGFR antibodies to enhance the efficacy of the inhibition of the growth of human cancer cells.

Furthermore, comparison of the anti-TGF-alpha antibody group to either the anti-EGF or the anti-EGFR groups shown that anti-TGF-alpha antibodies were more efficient than both anti-EGF and anti-EGFR antibodies at inhibiting the growth of human cancer cells known to produce TGF-alpha.

Moreover, comparison of the combination anti TGF-alpha+anti-PD-1 antibody group to either the combination anti-EGF+anti-PD-1 antibody or anti-EGFR+anti-PD-1 antibody groups shown that anti-TGF-alpha antibodies combined with anti-PD-1 antibodies were more efficient than both anti-EGF and anti-EGFR antibodies either alone or in combination with anti-PD-1 antibodies to inhibit the growth human cancer cells.

Example 11

In Vivo Evaluation of Therapeutic Efficacy of TGF-Alpha Antibodies in Combination with Anti-Pd-1 and/or Anti-CTLA4 Antibodies The therapeutic efficacy of TGF-alpha antibodies in combination with anti-PD-1 and/or anti-CTLA4 antibodies was tested in vivo, in a mouse xenograft model of melanoma.

C3H mice were subcutaneously injected with 0.5 million SW1 mouse tumor cells into the right flank (5 mice in each group). Seven days later, after the development of palpable tumors, mice were treated with control IgG antibodies, anti-TGF-alpha antibodies, anti-PD-1 antibodies+anti-CTLA4 antibodies or with anti-TGF-alpha antibodies+anti-PD-1 antibodies+anti-CTLA4 antibodies, respectively; injections were each antibody at 500 µg/antibody per mouse per injection, twice per week.

Figure 11:
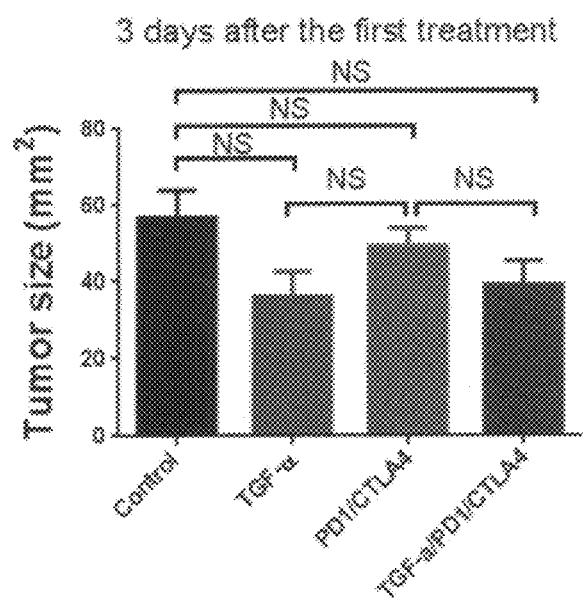
FIG. 11 shows the size of the tumors in 4 groups of mice 3 days after the first treatment with anti-TGF-alpha, anti-PD-1 and/or anti-CTLA4 antibodies. Control: untreated mice; TGF-α: mice treated with anti-TGF-alpha antibodies; PD-1/CTLA4: mice treated with anti-PD-1 antibodies+anti-CTLA4 antibodies; PD-1/CTLA4/TGF-α: mice treated with anti-PD-1 antibodies+anti-CTLA4 antibodies+anti-TGF-alpha antibodies; NS: non-significant.

As illustrated in FIG. 11, 3 days after the first treatment, the size of the tumors in animals treated with anti-TGF-alpha antibodies alone or in combination with PD-1 and CLTA4 antibodies was reduced as compared to the size of the tumors in control animals and in animals treated with PD-1 and CTLA4 antibodies only.

Figure 12A:
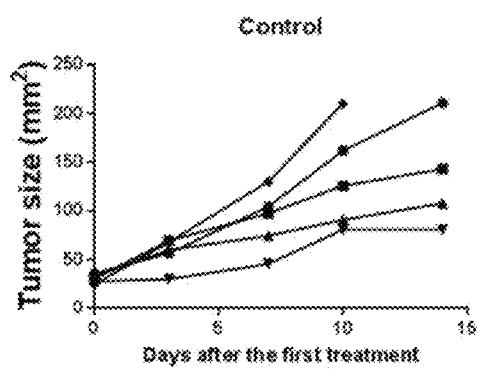
FIGS. 12A-12D show the evaluation of the size of the tumors in 4 groups of mice after the treatment with anti-TGF-alpha, anti-PD-1 and/or anti-CTLA4 antibodies. Specifically.
Figure 12B:
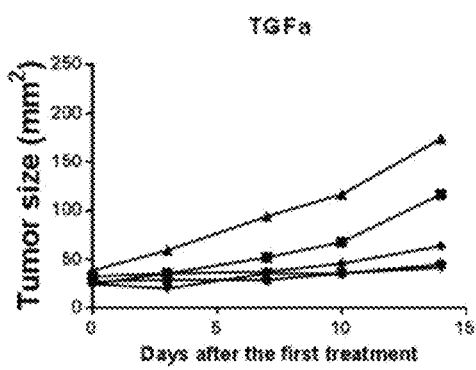
Figure 12C:
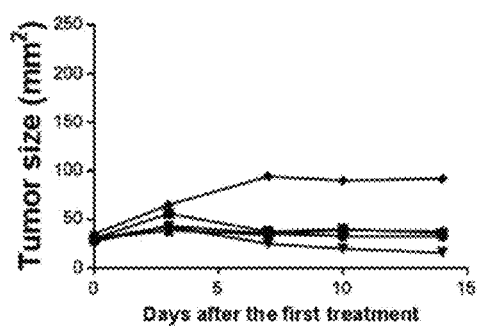
Figure 12D:
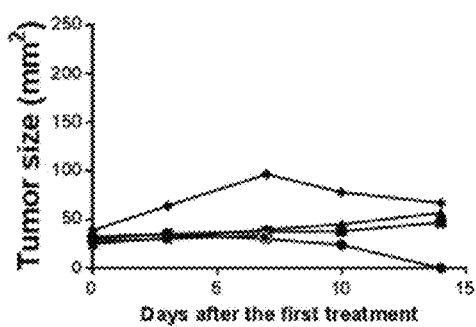

As shown in FIGS. 12A-12D, when the mice were treated with 500 µg of each antibody per injection, the combination of anti-TGF-alpha antibodies with anti-PD-1 and anti-CTLA4 antibodies (FIG. 12D) was more efficient at reducing tumor development than a treatment with anti-TGF-alpha antibodies alone (FIG. 12B), and more efficient than a treatment with a combination with anti-PD-1 and anti-CTLA4 antibodies (each at 500 µg) (FIG. 12C), as compared to the control, untreated mice (FIG. 12A).

Example 12

Figure 13A:
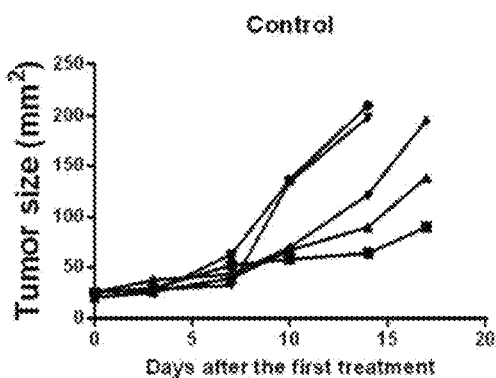
FIGS. 13A-13D show the evaluation of the size of the tumors in 4 groups of mice after the treatment with anti-TGF-alpha, and/or anti-PD-1 antibodies. Specifically.
Figure 13B:
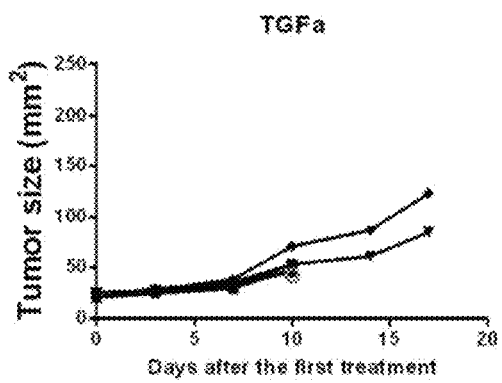
Figure 13C:
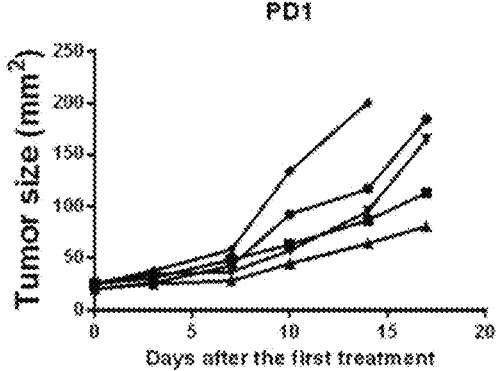
Figure 13D:
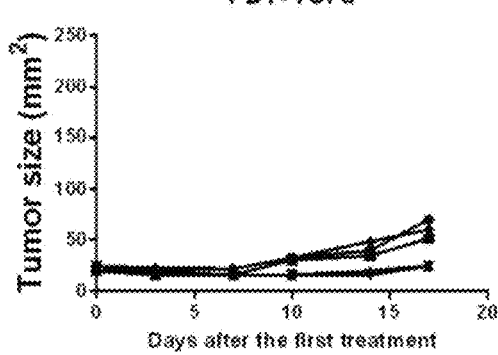

In Vivo Evaluation of Therapeutic Efficacy of TGF-Alpha Antibodies in Combination with Anti-Pd-1 Antibodies The therapeutic efficacy of TGF-alpha antibodies in combination with anti-PD-1 antibodies was evaluated in vivo, in mouse xenograft models of melanoma and lung cancer. C3H mice were subcutaneously injected with 0.5 million SW1 mouse tumor cells into the right flank (5 mice in each group). Seven days later, after the development of palpable tumors, mice were treated with control IgG antibodies, anti-TGF-alpha antibodies alone, anti-PD-1 antibodies alone or with a combination of anti-TGF-alpha antibodies+anti-PD-1 antibodies, respectively; injections were each antibody at 250 µg/antibody per mouse per injection, twice per week. As illustrated in FIGS. 13A-13D, when the mice received 250 µg of each antibody, twice weekly, it was found that the treatment with anti-TGF-alpha antibodies alone (FIG. 13B) was more efficient at inhibiting tumor growth than the treatment with anti-PD-1 antibodies alone (FIG. 13C). Additionally, the combination of anti-TGF-alpha antibodies with anti-PD-1 antibodies, injected twice weekly (250 µg of each antibody), successfully inhibited TGF-alpha-producing melanoma cells growth (FIG. 13D), as compared to the control untreated animals (FIG. 13A).

Figure 14:
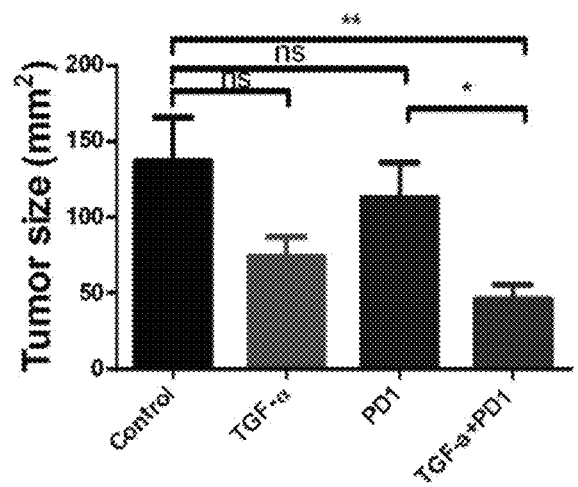
FIG. 14 shows the size of the tumors in 4 groups of mice 14 days after the first treatment with anti-TGF-alpha, and/or anti-PD-1. Control: untreated mice; TGF-α: mice treated with anti-TGF-alpha antibodies; PD-1: mice treated with anti-PD-1 antibodies; PD-1/TGF-α: mice treated with anti-PD-1 antibodies+anti-TGF-alpha antibodies; NS: non-significant; * and **: statistical significant difference.

In an alternative experiment, TGF-alpha-producing lung cancer cells were subcutaneously injected into mice as described above; and after the development of palpable tumors mice were treated with control IgG antibodies, anti-TGF-alpha antibodies alone, anti-PD-1 antibodies alone or with a combination of anti-TGF-alpha antibodies+anti-PD-1 antibodies, respectively. As illustrated in FIG. 14, the treatment with anti-TGF-alpha antibodies alone was more efficient at inhibiting tumor growth than the treatment with anti-PD-1 antibodies alone. Additionally, the combination of anti-TGF-alpha antibodies with anti-PD-1 antibodies successfully inhibited TGF-alpha-producing lung cancer cells growth.

Example 13

Evaluation of Efficacy of TGF-Alpha Antibodies to Induce T Cell Activation

To further evaluate the impact of an anti-TGF-alpha antibody treatment on cancer cells, the effect of the administration of anti-TGF-alpha antibodies on T cell activation was measured.

$5 \times 10^5$ SW1 cells were injected subcutaneously into a mouse. Seven days later the mouse was sacrificed when the tumor was about 5×5 mm, and the spleen was harvested. Splenocytes were isolated and $1 \times 10^6$ splenocytes were co-cultured with SW1 ($5 \times 10^3$ cells) in vitro with control IgG antibody conjugated beads, with anti-TGF-alpha antibody conjugated beads, with anti-EGF antibody conjugated beads, or with anti-EGFR antibody conjugated beads ($3 \times 10^6$ beads). Anti-PD1/CTLA4 antibodies were added to some wells to assess the effect of the combination therapy. Five days later, splenocytes were washed out from the plates and the beads were removed. The tumor killing effect (i.e., T cell activation) was investigated using flow cytometry analysis.

All together, the experiments described in Examples 10-13 highlighted the benefits of combining anti-immune checkpoint inhibitor antibodies (such as anti-PD-1 and anti-CTLA4 antibodies) to anti-TGF-alpha antibodies to synergize their effects and induce a more efficient inhibition of the growth of TGF-alpha-producing cancer cells.

Example 14

Development of a TGF-Alpha Vaccine Inducing High Titer of TGF-Alpha Antibodies

Based on the preclinical data collected using the injection of commercially available anti-TGF-alpha antibodies, an epitope of the protein would be isolated as the best antigen to be used in a vaccine to induce an immune response against autologous TGF-alpha.

This new vaccine would be capable of inducing a high titer of antibodies directed against TGF-alpha, there by inhibiting the TGF-alpha induced autocrine stimulatory pathway.

Following the methods know in the art for vaccine production, a viral vector, derived from example from a retrovirus, an adenovirus, an adeno-associated virus (AAV), a poxvirus or a herpes virus, encoding at least one antigen and at least one co-stimulatory molecule will be used. The antigen used would be recombinant TGF-alpha polypeptide or a fragment thereof to reflect the best epitopes identified using commercially available antibodies.

The vaccine would then be prepared to comprise a vector encoding the recombinant TGF-alpha or fragment and optionally a carrier protein, and an adjuvant to enhance the immune response induced by the vaccine.

This highly immunoreactive vaccine would be engineered to be capable of inducing high titer of TGF-alpha antibodies in its recipient, leading to the clearance of autologous TGF-alpha from the recipient circulation. This would be highly efficient to inhibit the TGF-alpha/EGFR interaction and the proliferation signaling pathway associated with it which is responsible for the autocrine growth stimulation leading to tumor growth in human cancers known to produce TGF-alpha.

Although the invention has been described with reference to the above examples, it will be understood that modifications and variations are encompassed within the spirit and scope of the invention. Accordingly, the invention is limited only by the following claims.

TABLE 4

| | TGF alpha sequences |
|---|---|
| SEQ ID NO.: 1 TGF-ALPHA splice variant 1 nucleic acid sequence | GTCAGCTGTGCCCCGGTCGCCGAGTGGCGAGGAGGTGACGGTAGCCGCCTT CCTATTTCCGCCCGGCGGGCAGCGCTGCGGGGCGAGTGCCAGCAGAGAGGC GCTCGGTCCTCCCTCCGCCCTCCCGCGCCGGGGGCAGGCCCTGCCTAGTCTG CGTCTTTTTCCCCCGCACCGCGGCGCCGCTCCGCCACTCGGGCACCGCAGGT AGGGCAGGAGGCTGGAGAGCCTGCTGCCCGCCCGCCCGTAAAATGGTCCCC TCGGCTGGACAGCTCGCCCTGTTCGCTCTGGGTATTGTGTTGGCTGCGTGCC AGGCCTTGGAGAACAGCACGTCCCCGCTGAGTGCAGACCCGCCCGTGGCTG CAGCAGTGGTGTCCCATTTTAATGACTGCCCAGATTCCCACACTCAGTT CTGCTTCCATGGAACCTGCAGGTTTTTGGTGCAGGAGGACAAGCCAGC ATGTGTCTGCCATTCTGGGTACGTTGGTGCACGCTGTGAGCATGCGGA CCTCCTGGCCGTGGTGGCTGCCAGCCAGAAGAAGCAGGCCATCACCGCCT TGGTGGTGGTCTCCATCGTGGCCCTGGCTGTCCTTATCATCACATGTGTGCT GATACACTGCTGCCAGGTCCGAAAACACTGTGAGTGGTGCCGGGCCCTCAT CTGCCGGCACGAGAAGCCCAGCGCCCTCCTGAAGGGAAGAACCGCTTGCTG CCACTCAGAAACAGTGGTCTGAAGAGCCCAGAGGAGGAGTTTGGCCAGGTG GACTGTGGCAGATCAATAAAGAAAGGCTTCTTCAGGACAGCACTGCCAGAG ATGCCTGGGTGTGCCACAGACCTTCCTACTTGGCCTGTAATCACCTGTGCAG CCTTTTGTGGGCCTTCAAAACTCTGTCAAGAACTCCGTCTGCTTGGGGTTATT CAGTGTGACCTAGAGAAGAAATCAGCGGACCACGATTTCAAGACTTGTTAA AAAAGAACTGCAAAGAGACGGACTCCTGTTCACCTAGGTGAGGTGTGTGCA GCAGTTGGTGTCTGAGTCCACATGTGTGCAGTTGTCTTCTGCCAGCCATGGA TTCCAGGCTATATATTTCTTTTTAATGGGCCACCTCCCCACAACAGAATTCTG CCCAACACAGGAGATTTCTATAGTTATTGTTTTCTGTCATTTGCCTACTGGGG AAGAAAGTGAAGGAGGGGAAACTGTTTAATATCACATGAAGACCCTAGCTT TAAGAGAAGCTGTATCCTCTAACCACGAGACCCTCAACCAGCCCAACATCTT CCATGGACACATGACATTGAAGACCATCCCAAGCTATCGCCACCCTTGGAG ATGATGTCTTATTTATTAGATGGATAATGGTTTTATTTTTAATCTCTTAAGTC AATGTAAAAGTATAAAACCCCTTCAGACTTCTACATTAATGATGTATGTGT TGCTGACTGAAAAGCTATACTGATTAGAAATGTCTGGCCTCTTCAAGACAGC TAAGGCTTGGGAAAAGTCTTCCAGGGTGCGGAGATGGAACCAGAGGCTGGG TTACTGGTAGGAATAAAGGTAGGGGTTCAGAAATGGTGCCATTGAAGCCAC AAAGCCGGTAAATGCCTCAATACGTTCTGGGAGAAAACTTAGCAAATCCAT CAGCAGGGATCTGTCCCCTCTGTTGGGGAGAGAGGAAGAGTGTGTGTGTCT ACACAGGATAAACCCAATACATATTGTACTGCTCAGTGATTAAATGGGTTCA CTTCCTCGTGAGCCCTCGGTAAGTATGTTTAGAAATAGAACATTAGCCACGA GCCATAGGCATTTCAGGCCAAATCCATGAAAGGGGGACCAGTCATTTATTTT CCATTTTGTTGCTTGGTTGGTTTGTTGCTTTATTTTTAAAAGGAGAAGTTTAA CTTTGCTATTTATTTTCGAGCACTAGGAAAACTATTCCAGTAATTTTTTTTTC CTCATTTCCATTCAGGATGCCGGCTTTATTAACAAAAACTCTAACAAGTCAC CTCCACTATGTGGGTCTTCCTTTCCCCTCAAGAGAAGGAGCAATTGTTCCCC TGAGCATCTGGGTCCATCTGACCCATGGGGCCTGCCTGTGAGAAACAGTGG GTCCCTTCAAATACATAGTGGATAGCTCATCCCTAGGAATTTTCATTAAAAT TTGGAAACAGAGTAATGAAGAAATAATATATAAACTCCTTATGTGAGGAAA TGCTACTAATATCTGAAAAGTGAAAGATTTCTATGTATTAACTCTTAAGTGC ACCTAGCTTATTACATCGTGAAAGGTACATTTAAAATATGTTAAATTGGCTT GAAATTTTCAGAGAATTTTGTCTTCCCCTAATTCTTCTTCCTTGGTCTGGAAG AACAATTTCTATGAATTTTCTCTTTATTTTTTTTATAATTCAGACAATTCTAT GACCCGTGTCTTCATTTTTGGCACTCTTATTTAACAATGCCACACCTGAAGC ACTTGGATCTGTTCAGAGCTGACCCCCTAGCAACGTAGTTGACACAGCTCCA GGTTTTTAAATTACTAAAATAAGTTCAAGTTTACATCCCTTGGGCCAGATAT GTGGGTTGAGGCTTGACTGTAGCATCCTGCTTAGAGACCAATCAACGGACA CTGGTTTTTAGACCTCTATCAATCAGTAGTTAGCATCCAAGAGACTTTGCAG AGGCGTAGGAATGAGGCTGGACAGATGGCGGAAGCAGAGGTTCCCTGCGA AGACTTGAGATTTAGTGTCTGTGAATGTTCTAGTTCCTAGGTCCAGCAAGTC ACACCTGCCAGTGCCCTCATCCTTATGCCTGTAACACACATGCAGTGAGAGG CCTCACATATACGCCTCCCTAGAAGTGCCTTCCAAGTCAGTCCTTTGGAAAC |

TABLE 4-continued

TGF alpha sequences

|  |  |
|---|---|
|  | CAGCAGGTCTGAAAAAGAGGCTGCATCAATGCAAGCCTGGTTGGACCATTG<br>TCCATGCCTCAGGATAGAACAGCCTGGCTTATTTGGGGATTTTTCTTCTAGA<br>AATCAAATGACTGATAAGCATTGGATCCCTCTGCCATTTAATGGCAATGGTA<br>GTCTTTGGTTAGCTGCAAAAATACTCCATTTCAAGTTAAAAATGCATCTTCT<br>AATCCATCTCTGCAAGCTCCCTGTGTTTCCTTGCCCTTTAGAAAATGAATTGT<br>TCACTACAATTAGAGAATCATTTAACATCCTGACCTGGTAAGCTGCCACACA<br>CCTGGCAGTGGGGAGCATCGCTGTTTCCAATGGCTCAGGAGACAATGAAAA<br>GCCCCCATTTAAAAAAATAACAAACATTTTTTAAAAGGCCTCCAATACTCTT<br>ATGGAGCCTGGATTTTTCCCACTGCTCTACAGGCTGTGACTTTTTTTAAGCAT<br>CCTGACAGGAAATGTTTTCTTCTACATGGAAAGATAGACAGCAGCCAACCC<br>TGATCTGGAAGACAGGGCCCCGGCTGGACACACGTGGAACCAAGCCAGGG<br>ATGGGCTGGCCATTGTGTCCCCGCAGGAGAGATGGGCAGAATGGCCCTAGA<br>GTTCTTTTCCCTGAGAAAGGAGAAAAGATGGGATTGCCACTCACCCACCC<br>ACACTGGTAAGGGAGGAGAATTTGTGCTTCTGGAGCTTCTCAAGGGATTGT<br>GTTTTGCAGGTACAGAAAACTGCCTGTTATCTTCAAGCCAGGTTTTCGAGGG<br>CACATGGGTCACCAGTTGCTTTTTCAGTCAATTTGGCCGGGATGGACTAATG<br>AGGCTCTAACACTGCTCAGGAGACCCCTGCCCTCTAGTTGGTTCTGGGCTTT<br>GATCTCTTCCAACCTGCCCAGTCACAGAAGGAGGAATGACTCAAATGCCCA<br>AAACCAAGAACACATTGCAGAAGTAAGACAAACATGTATATTTTTAAATGT<br>TCTAACATAAGACCTGTTCTCTCTAGCCATTGATTTACCAGGCTTTCTGAAA<br>GATCTAGTGGTTCACACAGAGAGAGAGAGTACTGAAAAAGCAACTCCTC<br>TTCTTAGTCTTAATAATTTACTAAAATGGTCAACTTTTCATTATCTTTATTAT<br>AATAAACCTGATGCTTTTTTTTAGAACTCCTTACTCTGATGTCTGTATATGTT<br>GCACTGAAAAGGTTAATATTTAATGTTTTAATTTATTTTGTGTGGTAAGTTA<br>ATTTTGATTTCTGTAATGTGTTAATGTGATTAGCAGTTATTTTCCTTAATATC<br>TGAATTATACTTAAAGAGTAGTGAGCAATATAAGACGCAATTGTGTTTTTCA<br>GTAATGTGCATTGTTATTGAGTTGTACTGTACCTTATTTGGAAGGATGAAGG<br>AATGAATCTTTTTTTCCTAAATCAA |
| SEQ ID NO.: 2<br>TGF-ALPHA splice<br>variant 2<br>nucleic acid<br>sequence | ACTCGGGCACCGCAGGTAGGGCAGGAGGCTGGAGAGCCTGCTGCCCGCCCG<br>CCCGTAAAATGGTCCCCTCGGCTGGACAGCTCGCCCTGTTCGCTCTGGGTAT<br>TGTGTTGGCTGCGTGCCAGGCCTTGGAGAACAGCACGTCCCCGCTGAGTGA<br>CCCCGCCCGTGGCTGCAGCAGTGGTGTCCCATTTTAATGACTGCCCAGATT<br>CCCACACTCAGTTCTGCTTCCATGGAACCTGCAGGTTTTTGGTGCAGGA<br>GGACAAGCCAGCATGTGTCTGCCATTCTGGGTACGTTGGTGCACGCTG<br>TGAGCATGCGGACCTCCTGGCCGTGGTGGCTGCCAGCCAGAAGAAGCAG<br>GCCATCACCGCCTTGGTGGTGGTCTCCATCGTGGCCCTGGCTGTCCTTATCA<br>TCACATGTGTGCTGATACACTGCTGCCAGGTCCGAAAACACTGTGAGTGGTG<br>CCGGGCCCTCATCTGCCGGCACGAGAAGCCCAGCGCCCTCCTGAAGGGAAG<br>AACCGCTTGCTGCCACTCAGAAACAGTGGTCTGAAGAGCCCAGAGGAGGAG<br>TTTGGCCAGGTGGACTGTGGCAGATCAATAAAGAAAGGCTTCTTCAGGACA<br>GCACTGCCAGAGATGCCTGGGTGTGCCACAGACCTTCCTACTTGGCCTGTAA<br>TCACCTGTGCAGCCTTTTGTGGGCCTTCAAAACTCTGTCAAGAACTCCGTCT<br>GCTTGGGGTTATTCAGTGTGACCTAGAGAAGAAATCAGCGGACCACGATTT<br>CAAGACTTGTTAAAAAAGAACTGCAAAGAGACGGACTCCTGTTCACCTAGG<br>TGAGGTGTGTGCAGCAGTTGGTGTCTGAGTCCACATGTGTGCAGTTGTCTTC<br>TGCCAGCCATGGATTCCAGGCTATATATTTCTTTTTAATGGGCCACCTCCCC<br>ACAACAGAATTCTGCCCAACACAGGAGATTTCTATAGTTATTGTTTTCTGTC<br>ATTTGCCTACTGGGGAAGAAAGTGAAGGAGGGGAAACTGTTTAATATCACA<br>TGAAGACCCTAGCTTTAAGAGAAGCTGTATCCTCTAACCACGAGACCCTCA<br>ACCAGCCCAACATCTTCCATGGACACATGACATTGAAGACCATCCCAAGCT<br>ATCGCCACCCTTGGAGATGATGTCTTATTTATTAGATGGATAATGGTTTTATT<br>TTTAATCTCTTAAGTCAATGTAAAAAGTATAAAACCCCTTCAGACTTCTA |
| SEQ ID NO.: 3<br>TGF-ALPHA splice<br>variant 3<br>nucleic acid<br>sequence | GCCCGCCTGGGAGAGTGGAGAGAAGCGAGTAGTCTCAATGGGTTGGCGCCT<br>GGGAGGCAAGGGGAGTCATTAAGAATGACAAAGAGGGGACTGTCCGGTCG<br>AGCGCCGAGGCTTCCCCGGGAAAGTGGCTGCCTGGGCCGTGCGTGAGAACA<br>CCTGGGAAGGGGAAGCGGAGTGTGAACGGGCTTGAACTTTAATCCGCCGCA<br>GCTGTGTGTCTGCTCAGACACATGCCTACACCTACCTGCTTACCTGGCTGCC<br>TCCAAGCCCGGCTCAGCCGGCGTCGCTGGCGTGTAGACTGGGCCGCCTCGG<br>AACGGGGGCCGGCGTCTAACCCTCTGGCCGGGTCTTGCCTGCGCCCCTTTGG<br>CACCCCCTGCCCACCTCTAAGCCCCAGCGACGAGCAGAGATGTTCAAGATC<br>GGCAGAGGCGCCCTCGATCTCTTTTCAGAGCTCTTGAGCTTTGGGGGTATTG<br>TGTTGGCTGCGTGCCAGGCCTTGGAGAACAGCACGTCCCCGCTGAGTGCAG<br>ACCCGCCCGTGGCTGCAGCAGTGGTGTCCCATTTTAATGACTGCCCAGAT<br>TCCCACACTCAGTTCTGCTTCCATGGAACCTGCAGGTTTTTGGTGCAGG<br>AGGACAAGCCAGCATGTGTCTGCCATTCTGGGTACGTTGGTGCACGCT<br>GTGAGCATGCGGACCTCCTGGCCGTGGTGGCTGCCAGCCAGAAGAAGCA<br>GGCCATCACCGCCTTGGTGGTGGTCTCCATCGTGGCCCTGGCTGTCCTTATC<br>ATCACATGTGTGCTGATACACTGCTGCCAGGTCCGAAAACACTGTGAGTGGT<br>GCCGGGCCCTCATCTGCCGGCACGAGAAGCCCAGCGCCCTCCTGAAGGGAA<br>GAACCGCTTGCTGCCACTCAGAAACAGTGGTCTGAAGAGCCCAGAGGAGGA<br>GTTTGGCCAGGTGGACTGTGGCAGATCAATAAAGAAAGGCTTCTTCAGGAC<br>AGCACTGCCAGAGATGCCTG |

TABLE 4-continued

TGF alpha sequences

| | |
|---|---|
| SEQ ID NO.: 4<br>TGF-ALPHA splice<br>variant 4<br>nucleic acid<br>sequence | AACACCTGGGAAGGGGAAGCGGAGTGTGAACGGGCTTGAACTTTAATCCGC<br>CGCAGCTGTGTGTCTGCTCAGACACATGCCTACACCTACCTGCTTACCTGGC<br>TGCCTCCAAGCCCGGCTCAGCCGGCGTCGCTGGCGTGTAGACTGGGCCGCCT<br>CGGAACGGGGGCCGGCGTCTAACCCTCTGGCCGGGTCTTGCCTGCGCCCTT<br>TGGCACCCCCTGCCCACCTCTAAGCCCCAGCGACGAGCAGAGATGTTCAAG<br>ATCGGCAGAGGCGCCCTCGATCTCTTTTCAGAGCTCTTGAGCTTTGGGGGTA<br>TTGTGTTGGCTGCGTGCCAGGCCTTGGAGAACAGCACGTCCCCGCTGAGTGA<br>CCCGCCCGTGGCTGCAGCAGTGGTGTCCCATTTTAATGACTGCCCAGATT<br>CCCACACTCAGTTCTGCTTCCATGGAACCTGCAGGTTTTTGGTGCAGGA<br>GGACAAGCCAGCATGTGTCTGCCATTCTGGGTACGTTGGTGCACGCTG<br>TGAGCATGCGGACCTCCTGGCCGTGGTGGCTGCCAGCCAGAAGAAGCAG<br>GCCATCACCGCCTTGGTGGTGGTCTCCATCGTGGCCCTGGCTGTCCTTATCA<br>TCACATGTGTGCTGATACACTGCTGCCAGGTCCGAAAACACTGTGAGTGGTG<br>CCGGGCCCTCATCTGCCGGCACGAGAAGCCCAGCGCCCTCCTGAAGGGAAG<br>AACCGCTTGCTGCCACTCAGAAACAGTGGTCTGAAGAGCCCAGAGGAGGAG<br>TTTGGCCAGGTGGACTGTGGCAGATCAATAAAGAAAGGCTTCTTCAGGACA<br>GCACTGCCAGAGATGCCTGGGTGTGCCACAGACCTTCCTACTTGGCCTGTAA<br>TCACCTGTGCAGCCTTTTGTGGGCCTTCAAAACTCTGTCAAGAACTCCGTCT<br>GCTTGGGGTTATTCAGTGTGACCTAGAGAAG |
| SEQ ID NO.: 5<br>TGF-ALPHA splice<br>variant 1<br>amino acid<br>sequence | MVPSAGQLALFALGIVLAACQALENSTSPLSADPPVAAAVVSHFNDCPDSHTQ<br>FCFHGTCRFLVQEDKPACVCHSGYVGARCEHADLLAVVAASQKKQAITAL<br>VVVSIVALAVLIITCVLIHCCQVRKHCEWCRALICRHEKPSALLKGRTACCHSET<br>VV |
| SEQ ID NO.: 6<br>TGF-ALPHA splice<br>variant 2<br>amino acid<br>sequence | MVPSAGQLALFALGIVLAACQALENSTSPLSDPPVAAAVVSHFNDCPDSHTQF<br>CFHGTCRFLVQEDKPACVCHSGYVGARCEHADLLAVVAASQKKQAITALV<br>VVSIVALAVLIITCVLIHCCQVRKHCEWCRALICRHEKPSALLKGRTACCHSETV<br>V |
| SEQ ID NO.: 7<br>TGF-ALPHA splice<br>variant 3<br>amino acid<br>sequence | MFKIGRGALDLFSELLSFGGIVLAACQALENSTSPLSADPPVAAAVVSHFNDCP<br>DSHTQFCFHGTCRFLVQEDKPACVCHSGYVGARCEHADLLAVVAASQKKQ<br>AITALVVVSIVALAVLIITCVLIHCCQVRKHCEWCRALICRHEKPSALLKGRTAC<br>CHSETVV |
| SEQ ID NO.: 8<br>TGF-ALPHA splice<br>variant 4<br>amino acid<br>sequence | MFKIGRGALDLFSELLSFGGIVLAACQALENSTSPLSDPPVAAAVVSHFNDCPD<br>SHTQFCFHGTCRFLVQEDKPACVCHSGYVGARCEHADLLAVVAASQKKQA<br>ITALVVVSIVALAVLIITCVLIHCCQVRKHCEWCRALICRHEKPSALLKGRTACC<br>HSETVV |
| SEQ ID NO.: 9<br>TGF-ALPHA Mature<br>nucleic acid<br>sequence | GTGTCCCATTTTAATGACTGCCCAGATTCCCACACTCAGTTCTGCTTCC<br>ATGGAACCTGCAGGTTTTTGGTGCAGGAGGACAAGCCAGCATGTGTCT<br>GCCATTCTGGGTACGTTGGTGCACGCTGTGAGCATGCGGACCTCCTGG<br>CCGTG |
| SEQ ID NO: 10<br>TGF-ALPHA Mature<br>amino acid<br>sequence | VVSHFNDCPDSHTQFCFHGTCRFLVQEDKPACVCHSGYVGARCEHADLLA |

What is claimed is:

1. A method of inhibiting growth of a solid tumor in a subject comprising administering to the subject a therapeutically effective amount of an immunotherapeutic treatment comprising an anti-transforming growth factor (TGF) alpha antibody or antigen-binding fragment thereof and a checkpoint inhibitor that inhibits programmed cell death protein (PD)-1 and, optionally, administering a further checkpoint inhibitor that inhibits cytotoxic T-lymphocyte-associated protein 4 (CTLA-4),
wherein the tumor is a TGF-alpha-producing tumor, and growth of the tumor detected fourteen days from administration is inhibited as compared to growth of the tumor after administration of either the TGF-alpha antibody or antigen-binding fragment thereof alone or administration of the checkpoint inhibitor that inhibits programmed cell death protein (PD)-1 alone, thereby inhibiting growth of the tumor in the subject.

2. The method of claim 1, wherein the cancer is selected from the group consisting of lung, stomach, prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, melanoma and urogenital tract.

3. The method of claim 2, wherein the cancer is breast, colon, stomach, lung or head and neck cancer.

4. The method of claim 1, further comprising administering to the subject a chemotherapeutic agent, radiation and/or an immune modulator either prior to, simultaneously with or following treatment with the TGF-alpha antibody or antigen-binding fragment thereof and/or the checkpoint inhibitor.

5. The method of claim 4, wherein the chemotherapeutic agent is selected from the group consisting of Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux, matuzumab, IMC-IIF 8, TheraCIM hR3, denosumab, Avastin, Humira, Herceptin, Remicade, rituximab, Synagis, Mylotarg, Raptiva, Tysabri, Zenapax, NeutroSpec, tocilizumab, ProstaScint, Bexxar, Zevalin, Xolair, MabThera, ReoPro, MabCampath, Simulect, LeukoScan, CEA-Scan (Verluma, Panorex, alemtuzumab, CDP 870, natalizumab, MGA271, lirilumab, BMS-986016, pembrolizumab, nivolumab, atezolizumab, avelumab, durvalumab, and iplimumab.

6. The method of claim 5, wherein the chemotherapeutic agent is pembrolizumab, nivolumab, atezolizumab, avelumab, durvalumab, and/or iplimumab.

7. The method of claim 4, wherein the immune modulator is selected from the group consisting of tocilizumab, CDP870, enteracept, adalimumab, anakinra, abatacept, infliximab, rituximab, golimumab, interferon beta-1a, peginterferon beta-1a, interferon beta-1b, glatiramer, mitoxantrone, natalizumab, fingolimod, teriflunomide, dimethyl fumarate, and alemtuzumab.

8. The method of claim 1, wherein the checkpoint inhibitor is an antibody or antigen-binding fragment thereof, a nucleic acid or a small molecule.

9. The method of claim 1, wherein the immunotherapeutic treatment comprises administration of an anti-TGF-alpha antibody or antigen-binding fragment thereof in combination with an anti-PD1 antibody or an anti-CTLA-4 antibody or antigen-binding fragment thereof.

10. The method of claim 1, wherein the antibody or antigen-binding fragment is selected from Fab, Fab' and F(ab')2, Fc fragments or Fc-fusion products, single-chain Fvs (scFv), disulfide-linked Fvs (sdfv) and fragments including either a VL or VH domain; diabodies, tribodies, Monoclonal monoclonal antibodies, human, humanized or chimeric antibodies, camelid or single chain antibodies.

11. The method of claim 1, wherein the tumor is resected prior to treatment.

12. The method of claim 1, wherein the subject is a human.

13. The method of claim 1, wherein the administration of the anti-TGF-alpha antibody or antigen-binding fragment thereof induces T-cell activation.

14. The method of claim 1, wherein the anti-TGF-alpha antibody or checkpoint inhibitor is administered by intravenous, oral, intramuscular, subcutaneous, intrathecal, infusion, transdermal, sublingual, buccal, rectal, vagina, ocular, optic, nasal, inhalation, nebulization, cutaneous, intraperitoneal or intratumoral administration.

15. The method of claim 1, wherein the anti-TGF-alpha antibody and the at least one checkpoint inhibitor are administered simultaneously with each other or sequentially.

16. The method of claim 1, wherein the anti-transforming growth factor (TGF) alpha antibody or antigen-binding fragment thereof is administered in combination with an inhibitor of programmed cell death protein (PD)-1 and an inhibitor of cytotoxic T-lymphocyte-associated protein 4 (CTLA-4).

\* \* \* \* \*

SEQUENCE LISTING

<160> NUMBER OF SEQ ID NOS: 10

<210> SEQ ID NO 1
<211> LENGTH: 4310
<212> TYPE: DNA
<213> ORGANISM: Homo sapiens
<220> FEATURE:
<221> NAME/KEY: misc_feature
<223> OTHER INFORMATION: TGF-ALPHA splice variant 1 nucleic acid
      sequence

<400> SEQUENCE: 1
gtcagctgtg cccggtcgc cgagtggcga ggaggtgacg gtagccgcct tcctatttcc      60
gcccggcggg cagcgctgcg gggcgagtgc cagcagagag gcgctcggtc ctccctccgc    120

```
cctcccgcgc cggggcagg ccctgcctag tctgcgtctt tttccccgc accgcggcgc    180 cgctccgcca ctcgggcacc gcaggtaggg caggaggctg gagagcctgc tgcccgcccg    240
cccgtaaaat ggtcccctcg gctggacagc tcgccctgtt cgctctgggt attgtgttgg    300
ctgcgtgcca ggccttggag aacagcacgt ccccgctgag tgcagacccg cccgtggctg    360
cagcagtggt gtcccatttt aatgactgcc cagattccca cactcagttc tgcttccatg    420
gaacctgcag ttttggtg caggaggaca agccagcatg tgtctgccat tctgggtacg    480
ttggtgcacg ctgtgagcat gcggacctcc tggccgtggt ggctgccagc cagaagaagc    540
aggccatcac cgccttggtg gtggtctcca tcgtggccct ggctgtcctt atcatcacat    600
gtgtgctgat acactgctgc caggtccgaa acactgtga gtggtgccgg ccctcatct    660 gccggcacga aagcccagc gccctcctga agggaagaac cgcttgctgc cactcagaaa    720
cagtggtctg aagagcccag aggaggagtt tggccaggtg gactgtggca gatcaataaa    780
gaaaggcttc ttcaggacag cactgccaga gatgcctggg tgtgccacag accttcctac    840
ttggcctgta atcacctgtg cagccttttg tgggccttca aaactctgtc aagaactccg    900
tctgcttggg gttattcagt gtgacctaga aagaaatca gcggaccacg atttcaagac    960
ttgttaaaaa agaactgcaa agagacggac tcctgttcac ctaggtgagg tgtgtgcagc   1020
agttggtgtc tgagtccaca tgtgtgcagt tgtcttctgc cagccatgga ttccaggcta   1080
tatatttctt tttaatgggc cacctcccca caacagaatt ctgcccaaca caggagattt   1140
ctatagttat tgttttctgt catttgccta ctggggaaga aagtgaagga gggaaactg   1200 tttaatatca catgaagacc ctagctttaa gagaagctgt atcctctaac cacgagaccc   1260
tcaaccagcc caacatcttc catggacaca tgacattgaa gaccatccca agctatcgcc   1320
acccttggag atgatgtctt atttattaga tggataatgg tttattttt aatctcttaa   1380 gtcaatgtaa aaagtataaa accccttcag acttctacat taatgatgta tgtgttgctg   1440
actgaaaagc tatactgatt agaaatgtct ggcctcttca agacagctaa ggcttgggaa   1500
aagtcttcca gggtgcggag atggaaccag aggctgggtt actggtagga ataaaggtag   1560
gggttcagaa atggtgccat tgaagccaca agccggtaa atgcctcaat acgttctggg   1620
agaaaactta gcaaatccat cagcagggat ctgtccctc tgttggggag agaggaagag   1680
tgtgtgtgtc tacacaggat aaacccaata catattgtac tgctcagtga ttaaatgggt   1740
tcacttcctc gtgagccctc ggtaagtatg tttagaaata gaacattagc cacgagccat   1800
aggcatttca ggccaaatcc atgaaagggg gaccagtcat ttatttcca ttttgttgct   1860 tggttggttt gttgctttat tttaaaagg agaagtttaa ctttgctatt tattttcgag   1920
cactaggaaa actattccag taattttttt ttcctcattt ccattcagga tgccggcttt   1980
attaacaaaa actctaacaa gtcacctcca ctatgtgggt cttccttttcc cctcaagaga   2040 aggagcaatt gttcccctga gcatctgggt ccatctgacc catggggcct gcctgtgaga   2100
aacagtgggt cccttcaaat acatagtgga tagctcatcc ctaggaattt tcattaaaat   2160
ttggaaacag agtaatgaag aaataatata taaactcctt atgtgaggaa atgctactaa   2220
tatctgaaaa gtgaaagatt tctatgtatt aactcttaag tgcacctagc ttattacatc   2280
gtgaaaggta catttaaaat atgttaaatt ggcttgaaat tttcagagaa ttttgtcttc   2340
ccctaattct tcttccttgg tctggaagaa caatttctat gaattttctc tttattttt   2400 tttataattc agacaattct atgacccgtg tcttcatttt tggcactctt atttaacaat   2460
```

| | |
|---|---|
| gccacacctg aagcacttgg atctgttcag agctgacccc ctagcaacgt agttgacaca | 2520 |
| gctccaggtt tttaaattac taaaataagt tcaagtttac atcccttggg ccagatatgt | 2580 |
| gggttgaggc ttgactgtag catcctgctt agagaccaat caacggacac tggtttttag | 2640 |
| acctctatca atcagtagtt agcatccaag agactttgca gaggcgtagg aatgaggctg | 2700 |
| gacagatggc ggaagcagag gttccctgcg aagacttgag atttagtgtc tgtgaatgtt | 2760 |
| ctagttccta ggtccagcaa gtcacacctg ccagtgccct catccttatg cctgtaacac | 2820 |
| acatgcagtg agaggcctca catatacgcc tccctagaag tgccttccaa gtcagtcctt | 2880 |
| tggaaaccag caggtctgaa aaagaggctg catcaatgca agcctggttg gaccattgtc | 2940 |
| catgcctcag gatagaacag cctggcttat ttggggattt ttcttctaga aatcaaatga | 3000 |
| ctgataagca ttggatccct ctgccattta atggcaatgg tagtctttgg ttagctgcaa | 3060 |
| aaatactcca tttcaagtta aaaatgcatc ttctaatcca tctctgcaag ctccctgtgt | 3120 |
| ttccttgccc tttagaaaat gaattgttca ctacaattag agaatcattt aacatcctga | 3180 |
| cctggtaagc tgccacacac ctggcagtgg ggagcatcgc tgtttccaat ggctcaggag | 3240 |
| acaatgaaaa gccccatttt aaaaaaataa caaacatttt ttaaaaggcc tccaatactc | 3300 |
| ttatggagcc tggattttc ccactgctct acaggctgtg actttttta agcatcctga | 3360 |
| caggaaatgt tttcttctac atggaaagat agacagcagc caaccctgat ctggaagaca | 3420 |
| gggccccggc tggacacacg tggaaccaag ccagggatgg gctggccatt gtgtccccgc | 3480 |
| aggagagatg ggcagaatgg ccctagagtt cttttccctg agaaaggaga aaaagatggg | 3540 |
| attgccactc acccacccac actggtaagg gaggagaatt tgtgcttctg gagcttctca | 3600 |
| agggattgtg ttttgcaggt acagaaaact gcctgttatc ttcaagccag gttttcgagg | 3660 |
| gcacatgggt caccagttgc ttttcagtc aatttggccg ggatggacta atgaggctct | 3720 |
| aacactgctc aggagacccc tgccctctag ttggttctgg gctttgatct cttccaacct | 3780 |
| gcccagtcac agaaggagga atgactcaaa tgcccaaaac caagaacaca ttgcagaagt | 3840 |
| aagacaaaca tgtatatttt taaatgttct aacataagac ctgttctctc tagccattga | 3900 |
| tttaccaggc tttctgaaag atctagtggt tcacacagag agagagagag tactgaaaaa | 3960 |
| gcaactcctc ttcttagtct taataattta ctaaaatggt caacttttca ttatctttat | 4020 |
| tataataaac ctgatgcttt tttttagaac tccttactct gatgtctgta tatgttgcac | 4080 |
| tgaaaaggtt aatatttaat gttttaattt attttgtgtg gtaagttaat tttgattct | 4140 |
| gtaatgtgtt aatgtgatta gcagttattt tccttaatat ctgaattata cttaaagagt | 4200 |
| agtgagcaat ataagacgca attgtgtttt tcagtaatgt gcattgttat tgagttgtac | 4260 |
| tgtaccttat ttggaaggat gaaggaatga atctttttt cctaaatcaa | 4310 |

<210> SEQ ID NO 2
<211> LENGTH: 1225
<212> TYPE: DNA
<213> ORGANISM: Homo sapiens
<220> FEATURE:
<221> NAME/KEY: misc_feature
<223> OTHER INFORMATION: TGF-ALPHA splice variant 2 nucleic acid
      sequence

<400> SEQUENCE: 2

| | |
|---|---|
| actcgggcac cgcaggtagg gcaggaggct ggagagcctg ctgcccgccc gcccgtaaaa | 60 |
| tggtcccctc ggctggacag ctcgcccgt tcgctctggg tattgtgttg gctgcgtgcc | 120 |
| aggccttgga gaacagcacg tccccgctga gtgacccgcc cgtggctgca gcagtggtgt | 180 |

```
cccattttaa tgactgccca gattcccaca ctcagttctg cttccatgga acctgcaggt    240
ttttggtgca ggaggacaag ccagcatgtg tctgccattc tgggtacgtt ggtgcacgct    300
gtgagcatgc ggacctcctg gccgtggtgg ctgccagcca agaagcagg ccatcaccg      360 ccttggtggt ggtctccatc gtggccctgg ctgtccttat catcacatgt gtgctgatac    420
actgctgcca ggtccgaaaa cactgtgagt ggtgccgggc cctcatctgc cggcacgaga    480
agcccagcgc cctcctgaag ggaagaaccg cttgctgcca ctcagaaaca gtggtctgaa    540
gagcccagag gaggagtttg gccaggtgga ctgtggcaga tcaataaaga aaggcttctt    600
caggacagca ctgccagaga tgcctgggtg tgccacagac cttcctactt ggcctgtaat    660
cacctgtgca gccttttgtg ggccttcaaa actctgtcaa gaactccgtc tgcttggggt    720
tattcagtgt gacctagaga agaaatcagc ggaccacgat ttcaagactt gttaaaaaag    780
aactgcaaag agacggactc ctgttcacct aggtgaggtg tgtgcagcag ttggtgtctg    840
agtccacatg tgtgcagttg tcttctgcca gccatggatt ccaggctata tatttctttt    900
taatgggcca cctccccaca acagaattct gcccaacaca ggagatttct atagttattg    960
ttttctgtca tttgcctact ggggaagaaa gtgaaggagg ggaaactgtt taatatcaca   1020
tgaagaccct agctttaaga gaagctgtat cctctaacca cgagaccctc aaccagccca   1080
acatcttcca tggacacatg acattgaaga ccatcccaag ctatcgccac ccttggagat   1140
gatgtcttat ttattagatg gataatggtt ttatttttaa tctcttaagt caatgtaaaa   1200
agtataaaac cccttcagac ttcta                                          1225

<210> SEQ ID NO 3
<211> LENGTH: 985
<212> TYPE: DNA
<213> ORGANISM: Homo sapiens
<220> FEATURE:
<221> NAME/KEY: misc_feature
<223> OTHER INFORMATION: TGF-ALPHA splice variant 3 nucleic acid
      sequence

<400> SEQUENCE: 3
gcccgcctgg gagagtggag agaagcgagt agtctcaatg ggttggcgcc tgggaggcaa     60
ggggagtcat taagaatgac aaagagggga ctgtccggtc gagcgccgag gcttccccgg   120
gaaagtggct gcctgggccg tgcgtgagaa cacctgggaa ggggaagcgg agtgtgaacg   180
ggcttgaact ttaatccgcc gcagctgtgt gtctgctcag acacatgcct acacctacct   240
gcttacctgc tgcctccaa gcccggctca gccggcgtcg ctggcgtgta gactgggccg    300
cctcggaacg ggggccggcg tctaaccctc tggccgggtc ttgcctgcgc cctttggca    360 cccccctgccc acctctaagc cccagcgacg agcagagatg ttcaagatcg gcagaggcgc   420
cctcgatctc ttttcagagc tcttgagctt tgggggtatt gtgttggctg cgtgccaggc   480
cttggagaac agcacgtccc cgctgagtgc agacccgccc gtggctgcag cagtggtgtc   540
ccattttaat gactgcccag attcccacac tcagttctgc ttccatggaa cctgcaggtt    600
tttggtgcag gaggacaagc cagcatgtgt ctgccattct gggtacgttg gtgcacgctg    660
tgagcatgcg gacctcctgg ccgtggtggc tgccagccaa agaagcagg ccatcaccgc     720 cttggtggtg gtctccatcg tggccctggc tgtccttatc atcacatgtg tgctgataca    780
ctgctgccag gtccgaaaac actgtgagtg gtgccgggcc ctcatctgcc ggcacgagaa    840
gcccagcgcc ctcctgaagg gaagaaccgc ttgctgccac tcagaaacag tggtctgaag   900
```
agcccagagg aggagtttgg ccaggtggac tgtggcagat caataaagaa aggcttcttc    960
aggacagcac tgccagagat gcctg                                         985

<210> SEQ ID NO 4
<211> LENGTH: 950
<212> TYPE: DNA
<213> ORGANISM: Homo sapiens
<220> FEATURE:
<221> NAME/KEY: misc_feature
<223> OTHER INFORMATION: TGF-ALPHA splice variant 4 nucleic acid
      sequence

<400> SEQUENCE: 4
aacacctggg aaggggaagc ggagtgtgaa cgggcttgaa ctttaatccg ccgcagctgt     60
gtgtctgctc agacacatgc ctacacctac ctgcttacct ggctgcctcc aagcccggct    120
cagccggcgt cgctggcgtg tagactgggc cgcctcggaa cggggggccgg cgtctaaccc    180 tctggccggg tcttgcctgc gccccttttgg caccccctgc ccacctctaa gcccagcga    240 cgagcagaga tgttcaagat cggcagaggc gccctcgatc tcttttcaga gctcttgagc    300
tttgggggta ttgtgttggc tgcgtgccag gccttggaga acagcacgtc cccgctgagt    360
gacccgcccg tggctgcagc agtggtgtcc cattttaatg actgcccaga ttcccacact    420
cagttctgct ccatggaac ctgcaggttt ttggtgcagg aggacaagcc agcatgtgtc    480
tgccattctg gtacgttgg tgcacgctgt gagcatgcgg acctcctggc cgtggtggct    540
gccagccaga gaagcaggc catcaccgcc ttggtggtgg tctccatcgt ggccctggct    600
gtccttatca tcacatgtgt gctgatacac tgctgccagg tccgaaaaca ctgtgagtgg    660
tgccgggccc tcatctgccg gcacgagaag cccagcgccc tcctgaaggg aagaaccgct    720
tgctgccact cagaaacagt ggtctgaaga gcccagagga ggagtttggc caggtggact    780
gtggcagatc aataaagaaa ggcttcttca ggacagcact gccagagatg cctgggtgtg    840
ccacagacct tcctacttgg cctgtaatca cctgtgcagc cttttgtggg ccttcaaaac    900
tctgtcaaga actccgtctg cttggggtta ttcagtgtga cctagagaag    950

<210> SEQ ID NO 5
<211> LENGTH: 160
<212> TYPE: PRT
<213> ORGANISM: Homo sapiens
<220> FEATURE:
<221> NAME/KEY: misc_feature
<223> OTHER INFORMATION: TGF-ALPHA splice variant 1 amino acid sequence

<400> SEQUENCE: 5

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
                20                  25                  30

Asp Pro Pro Val Ala Ala Ala Val Val Ser His Phe Asn Asp Cys Pro
            35                  40                  45

Asp Ser His Thr Gln Phe Cys Phe His Gly Thr Cys Arg Phe Leu Val
        50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Val Ala Ala Ser Gln Lys
                85                  90                  95

Lys Gln Ala Ile Thr Ala Leu Val Val Val Ser Ile Val Ala Leu Ala
            100                 105                 110

Val Leu Ile Ile Thr Cys Val Leu Ile His Cys Cys Gln Val Arg Lys
                115                 120                 125

His Cys Glu Trp Cys Arg Ala Leu Ile Cys Arg His Glu Lys Pro Ser
        130                 135                 140

Ala Leu Leu Lys Gly Arg Thr Ala Cys Cys His Ser Glu Thr Val Val
145                 150                 155                 160

<210> SEQ ID NO 6
<211> LENGTH: 159
<212> TYPE: PRT
<213> ORGANISM: Homo sapiens
<220> FEATURE:
<221> NAME/KEY: misc_feature
<223> OTHER INFORMATION: TGF-ALPHA splice variant 2 amino acid sequence

<400> SEQUENCE: 6

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Asp
                20                  25                  30

Pro Pro Val Ala Ala Val Val Ser His Phe Asn Asp Cys Pro Asp
        35                  40                  45

Ser His Thr Gln Phe Cys Phe His Gly Thr Cys Arg Phe Leu Val Gln
    50                  55                  60

Glu Asp Lys Pro Ala Cys Val Cys His Ser Gly Tyr Val Gly Ala Arg
65                  70                  75                  80

Cys Glu His Ala Asp Leu Leu Ala Val Val Ala Ala Ser Gln Lys Lys
                85                  90                  95

Gln Ala Ile Thr Ala Leu Val Val Val Ser Ile Val Ala Leu Ala Val
                100                 105                 110

Leu Ile Ile Thr Cys Val Leu Ile His Cys Cys Gln Val Arg Lys His
                115                 120                 125

Cys Glu Trp Cys Arg Ala Leu Ile Cys Arg His Glu Lys Pro Ser Ala
        130                 135                 140

Leu Leu Lys Gly Arg Thr Ala Cys Cys His Ser Glu Thr Val Val
145                 150                 155

<210> SEQ ID NO 7
<211> LENGTH: 166
<212> TYPE: PRT
<213> ORGANISM: Homo sapiens
<220> FEATURE:
<221> NAME/KEY: misc_feature
<223> OTHER INFORMATION: TGF-ALPHA splice variant 3 amino acid sequence

<400> SEQUENCE: 7

Met Phe Lys Ile Gly Arg Gly Ala Leu Asp Leu Phe Ser Glu Leu Leu
1               5                   10                  15

Ser Phe Gly Gly Ile Val Leu Ala Ala Cys Gln Ala Leu Glu Asn Ser
                20                  25                  30

Thr Ser Pro Leu Ser Ala Asp Pro Val Ala Ala Val Val Ser
        35                  40                  45

His Phe Asn Asp Cys Pro Asp Ser His Thr Gln Phe Cys Phe His Gly
    50                  55                  60

Thr Cys Arg Phe Leu Val Gln Glu Asp Lys Pro Ala Cys Val Cys His
65                  70                  75                  80

Ser Gly Tyr Val Gly Ala Arg Cys Glu His Ala Asp Leu Leu Ala Val
                85                  90                  95

```
Val Ala Ala Ser Gln Lys Lys Gln Ala Ile Thr Ala Leu Val Val Val
            100                 105                 110

Ser Ile Val Ala Leu Ala Val Leu Ile Ile Thr Cys Val Leu Ile His
            115                 120                 125

Cys Cys Gln Val Arg Lys His Cys Glu Trp Cys Arg Ala Leu Ile Cys
    130                 135                 140

Arg His Glu Lys Pro Ser Ala Leu Leu Lys Gly Arg Thr Ala Cys Cys
145                 150                 155                 160

His Ser Glu Thr Val Val
                165

<210> SEQ ID NO 8
<211> LENGTH: 165
<212> TYPE: PRT
<213> ORGANISM: Homo sapiens
<220> FEATURE:
<221> NAME/KEY: misc_feature
<223> OTHER INFORMATION: TGF-ALPHA splice variant 4 amino acid sequence

<400> SEQUENCE: 8

Met Phe Lys Ile Gly Arg Gly Ala Leu Asp Leu Phe Ser Glu Leu Leu
1               5                   10                  15

Ser Phe Gly Gly Ile Val Leu Ala Ala Cys Gln Ala Leu Glu Asn Ser
            20                  25                  30

Thr Ser Pro Leu Ser Asp Pro Pro Val Ala Ala Ala Val Ser His
            35                  40                  45

Phe Asn Asp Cys Pro Asp Ser His Thr Gln Phe Cys Phe His Gly Thr
    50                  55                  60

Cys Arg Phe Leu Val Gln Glu Asp Lys Pro Ala Cys Val Cys His Ser
65                  70                  75                  80

Gly Tyr Val Gly Ala Arg Cys Glu His Ala Asp Leu Leu Ala Val Val
                85                  90                  95

Ala Ala Ser Gln Lys Lys Gln Ala Ile Thr Ala Leu Val Val Val Ser
            100                 105                 110

Ile Val Ala Leu Ala Val Leu Ile Ile Thr Cys Val Leu Ile His Cys
            115                 120                 125

Cys Gln Val Arg Lys His Cys Glu Trp Cys Arg Ala Leu Ile Cys Arg
    130                 135                 140

His Glu Lys Pro Ser Ala Leu Leu Lys Gly Arg Thr Ala Cys Cys His
145                 150                 155                 160

Ser Glu Thr Val Val
                165

<210> SEQ ID NO 9
<211> LENGTH: 150
<212> TYPE: DNA
<213> ORGANISM: Homo sapiens
<220> FEATURE:
<221> NAME/KEY: misc_feature
<223> OTHER INFORMATION: TGF-ALPHA Mature nucleic acid sequence

<400> SEQUENCE: 9
gtgtcccatt ttaatgactg cccagattcc cacactcagt tctgcttcca tggaacctgc      60 aggttttttgg tgcaggagga caagccagca tgtgtctgcc attctgggta cgttggtgca    120
cgctgtgagc atgcggacct cctggccgtg                                      150

<210> SEQ ID NO 10
```

```
<211> LENGTH: 50
<212> TYPE: PRT
<213> ORGANISM: Homo sapiens
<220> FEATURE:
<221> NAME/KEY: misc_feature
<223> OTHER INFORMATION: TGF-ALPHA Mature amino acid sequence

<400> SEQUENCE: 10

Val Val Ser His Phe Asn Asp Cys Pro Asp Ser His Thr Gln Phe Cys
1               5                   10                  15

Phe His Gly Thr Cys Arg Phe Leu Val Gln Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50
```